United States Patent [19]

Smith

[11] Patent Number: 4,783,750
[45] Date of Patent: Nov. 8, 1988

[54] DETERMINATION OF OXYGEN UPTAKE RATE IN WASTEWATER TREATMENT PLANTS

[75] Inventor: Daniel W. Smith, Edmonton, Canada

[73] Assignee: The Governors of the University of Alberta, Edmonton, Canada

[21] Appl. No.: 907,326

[22] Filed: Sep. 15, 1986

[51] Int. Cl.$^4$ .............................................. G06F 15/46
[52] U.S. Cl. ................................... 364/497; 210/614; 210/626; 364/500
[58] Field of Search ................ 364/497, 500; 210/614, 210/626

[56] References Cited

U.S. PATENT DOCUMENTS

| | | | |
|---|---|---|---|
| 3,684,702 | 8/1972 | Hartmann | 364/500 X |
| 3,926,738 | 12/1975 | Wilson | 361/500 X |
| 3,986,932 | 10/1976 | Brushwyler et al. | 210/614 X |
| 4,329,232 | 5/1982 | McKenna | 210/614 |
| 4,424,559 | 1/1984 | Lorincz et al. | 364/500 X |
| 4,442,005 | 4/1984 | Breider | 210/614 |
| 4,620,930 | 11/1986 | McDowell | 210/614 |

FOREIGN PATENT DOCUMENTS

| | | | |
|---|---|---|---|
| 54-127155 | 10/1979 | Japan | 210/614 |
| 54-127154 | 10/1979 | Japan | 210/614 |
| 0043292 | 12/1983 | Japan | 210/614 |

*Primary Examiner*—R. R. Kucia
*Attorney, Agent, or Firm*—Shoemaker and Mattare, Ltd.

[57] ABSTRACT

A method and apparatus for determining the oxygen uptake rate of bacteria in a body of liquid incorporates withdrawing a sample of the liquid into a chamber where a dissolved oxygen probe is located, the probe outputting a signal which is a function of the amount of dissolved oxygen in the sample. The sample is aerated, and a computer is used to sample the signal at regular intervals to produce a series of time-separated values corresponding to the sampled signals, the values representing the dissolved oxygen in the sample at the timed intervals. Repeated samples can be taken, so that the O.U.R. can be monitored on a continuing basis. The O.U.R. information can be used to control the rate of aeration in a tank, or to control the rate of recycling of activated sludge from the downstream to the upstream end of the tank.

10 Claims, 21 Drawing Sheets

DETERMINATION OF OXYGEN UPTAKE RATE IN WASTEWATER TREATMENT PLANTS

This invention relates generally to wastewater treatment plants of the kind used typically to treat wastewater from a residential or industrial area.

BACKGROUND OF THIS INVENTION

Generally speaking, wastewater treatment plants of the kind utilized in cities and towns in North America typically incorporate a number of tanks through which the wastewater is passed, and where various operations are performed. Virtually all such treatment plants utilize bacterial action to break down organics which the wastewater contains. The bacteria utilized are obligate aerobes, which means that there is a necessity to provide an on-going supply of oxygen to the bacteria in those tanks which are designated for the digestion or breaking down of organic materials. The organic materials and the bacteria form what is known as activated sludge, and the term "activated sludge wastewater treatment tanks", is normally applied to the containers where such digestion takes place Depending upon design, other tanks in a typical plant may be used as settling tanks to allow separation of sludge from clarified liquor The present invention focuses particularly upon the wastewater treatment tanks utilizing activating sludge, and it is appropriate here to discuss several of the problems associated with conventional such tanks.

The rate at which the bacteria in a wastewater treatment tank consume oxygen while they digest the organics is referred to as the "oxygen uptake rate" or O.U.R. In the monitoring procedure for a wastewater treatment plant, one of the essential factors which must be determined on a regular basis is the O.U.R. The O.U.R. provides an index of bacterial activity, and that activity can vary from time to time for several reasons. One reason relates to the amount of incoming organics at different parts of the daily cycle. At night, when most users of the wastewater system are seeeping, there is normally a drop-off in the amount of organics arriving at the activated sludge treatment tanks. In many cases, this will lead to a decrease in the O.U.R. during the nighttime hours.

Another reason for a change in the O.U.R. may be that, for some reason, bacteria have been removed from a tank faster than the natural replenishment rate of the bacterial colonies. In another example, the reason for a decrease in the O.U.R. may be the influx of toxic chemical materials (for example from industrial processes) which have an inhibiting or lethal effect on the bacteria.

With regard to the variation of incoming organics, it will be appreciated that conventional plants are not equipped to take advantage of the natural decrease during the nighttime hours, should this take place, since most typical plants are designed to blow air into the activated sludge treatment tanks at a given rate, which is higher than that calculated to provide the maximum possible oxygen demand. In other words, most typical plants have a blower system for blowing air into the activated sludge treatment tanks at a single rate, and the compressors are expected to run continuously at that rate. However, this leads to an over-oxygenation of the liquid in a treatment tank during those periods when the incoming organics are reduced substantially. It will be appreciated that it requires a substantial amount of energy to blow air into the treatment tanks, since this must be done under a head of from 5 feet to 10 feet (depending on the depth of the nozzles), and therefore the air must be moved against a specific superatmospheric pressure. The electrical energy required to move all of this air can represent a cost in the millions of dollars per year, for a given city of substantial size. A considerable saving in expenditure could be effected if the rate at which air is blown into the treatment tanks could be regulated in accordance with the amount of incoming organic material, in such a way that the oxygenation of the liquid more closely approximates the actual bacterial activity.

As previously indicated, it sometimes happens that the activated sludge in a treatment tank is removed at a rate faster than the natural regeneration rate of the bacterial colonies, resulting in a shortfall of the bacterial agent, and hence a reduction in the O.U.R. This may happen despite the fact that incoming organics are at the normal daytime level, which normally would produce a higher O.U.R. One of the responses to this situation is to return settled sludge into the system, to replenish the bacterial agent.

In view of the foregoing discussion, it is an object of an aspect of this invention to provide a method and apparatus for automatically determining the O.U.R. in an activated sludge wastewater treatment tank.

It is an object of another aspect of this invention to provide a method and apparatus for determining the O.U.R. of an activated sludge wastewater treatment tank on a regular and continuing basis, so that any substantial variations of the O.U.R. can be observed.

It is an object of a further aspect of this invention to provide a method and apparatus which utilizes a regularly determined O.U.R. to regulate the rate at which air is pumped into an activated sludge wastewater treatment tank.

Finally, it is an object of yet another aspect of this invention to provide a method and apparatus which utilizes a regularly and automatically computed O.U.R. to control the rate at which settled sludge is returned into the system.

To round out the prior art, reference may be had to the following patents:

U.S. Pat. No. 3,607,735, issued Sept. 21, 1971 to Hover et al;

U.S. Pat. No. 4,256,575, issued Mar. 17, 1981 to Garrett et al;

U.S. Pat. No. 3,909,409, issued Sept. 30, 1975 to Lange et al;

U.S. Pat. No. 4,416,781, issued Nov. 22, 1983 to Bailey et al;

U.S. Pat. No. 4,171,263, issued Oct. 16, 1979 to Roberts, et al;

U.S. Pat. No. 3,925,721, issued Dec. 9, 1975 to Petroff;

U.S. Pat. No. 3,547,811, issued Dec. 15, 1970 to McWhirter;

U.S. Pat. No. 3,872,003, issued Mar. 18, 1975 to Walker;

U.S. Pat. No. 3,823,728, issued July 16, 1974 to Burris.

GENERAL DESCRIPTION OF THIS INVENTION

Accordingly, there is described herein a method of determining the oxygen uptake rate of bacteria in a body of liquid. The method includes first withdrawing a sample of the liquid into a chamber in which is located a dissolved oxygen (D.O.) probe which outputs a signal which is a function of the amount of dissolved oxygen in the sample adjacent the probe. The sample is then aerated, and a computer is utilized to sample the signal at regular intervals and to produce a series of time-separated values corresponding to the sampled signals, which values represent the dissolved oxygen in the sample at timed intervals.

There is further described a method of determining the oxygen uptake rate of bacteria in a body of liquid, and changes in such rate. The method incorporates the steps enumerated above, and those steps are repeated a plurality of times to generate a plurality of sets of such values. Computer means then calculates, for each set of the values, the rate at which the oxygen content of the sample decreases with time.

In one aspect, the present invention provides a method of controlling the aeration rate of an activated sludge wastewater treatment tank. The foregoing steps are carried out to generate a plurality of sets of values, each set corresponding to a sample of the liquid in the tank, the samples being withdrawn at time-separated intervals. Then, whenever for any set of values the rate of decrease of the oxygen content is below a predetermined value, the aeration rate for the treatment tank is decreased.

In another aspect, this invention provides a method of controlling the rate at which settled sludge is removed from a tank and readmitted to the system to replenish the bacterial agents which function to break down organic materials in the wastewater. The method incorporates the steps enumerated earlier, to generate a plurality of sets of vlaues, each set corresponding to a different sample withdrawn from the tank, the values of each set demonstrating the rate at which the oxygen content of the particular sample decreases with time. Then, whenever for any set of values the rate of decrease of the oxygen content is below a predetermined value, the rate at which settled sludge is readmitted to the system can be increased.

GENERAL DESCRIPTION OF THE DRAWINGS

One embodiment of this invention is illustrated in the accompanying drawings, in which.

DETAILED DESCRIPTION OF THE DRAWINGS

Figure 1:
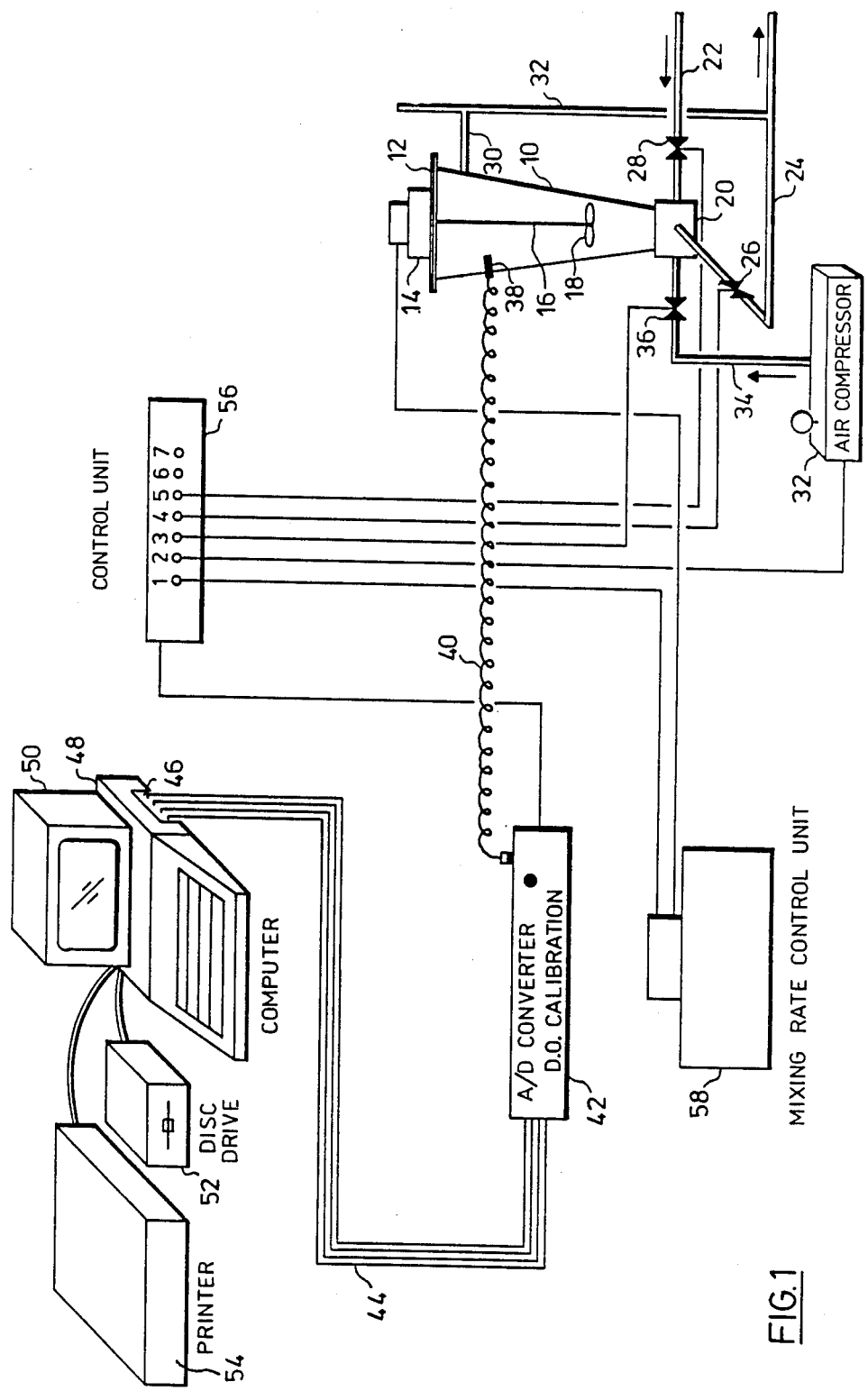
FIG. 1 is a schematic view of a microprocessor-controlled sampling system for determining the O.U.R.

Attention is first directed to FIG. 1, in which an upwardly diverging conical container 10 defines an internal chamber which is closed at the top by a cap 12 on which is mounted a mixing motor 14 adapted to rotate a spindle 16 having a mixing propeller 18 mounted at its lower end. The container 10 is supported on a base 20 and communicates with a recess in the base 20. A first conduit 22 continuously brings mixed liquor and solids from an activated sludge wastewater treatment tank in a typical wastewater plant to the recess in the base 20, and a further conduit 24 is connected to the recess in the base 20 through a solenoid valve 26 such that, when the valve 26 is open, the mixed liquor and solids arriving along the conduit 22 is continuously removed along the conduit 24 and recirculated to the tank. The conduit 22 has a solenoid valve 28 which can be closed to halt flow along the conduit 22.

Near the top of the container 10 is an outflow conduit 30 which communicates with a standpipe 32 which in turn communicates with the conduit 24. The conduit 30 acts as an overflow conduit, and establishes the level to which liquid can rise in the container 10.

An air compressor 32 is provided, and an air pipe 34 is adapted to carry compressed air from the compressor 32 to the base 20, from where it can bubble up through a sample in the container 10. The tube 34 has a further solenoid valve 36.

Mounted in the conical wall of the container 10 is a dissolved oxygen (D.O.) probe 38 of conventional nature, which is adapted to output an analog signal which is a function of the amount of oxygen dissolved in a liquid sample in which the probe 38 is immersed.

Several suitable D.O. probes are available on the market, and one such is manufactured by Yellow Springs Instrument Co., Inc. (YSI). YSI produces several probes in the 5700 series, which would be suitable with the present process. Within the probe is a thin permeable membrane stretched over the sensor to isolate the sensor elements from the environment, but to allow gases to enter. The sensor consists of a gold cathode and a silver anode. When a polarizing voltage is applied across the electrodes, oxygen that has passed through the membrane reacts at the cathode to cause a current to flow. The membrane passes oxygen at a rate proportional to the pressure difference across it. Since oxygen is rapidly consumed at the cathode, it can be assumed that the oxygen pressure under the membrane is zero. Hence, the force causing the oxygen to diffuse through the membrane is proportional to the absolute pressure of oxygen outside the membrane. As the oxygen pressure increases, more oxygen diffuses through the membrane, and more current flows through the sensor. Conversely, a lower pressure results in less current. A typical polarizing voltage would be 0.8 volts, and current flow is in the range of a few microamperes.

The analog (amperage) signal from the probe 38 is carried along the wire 40 to an analog-to-digital converter 42, from which output lines 44 pass to the input 46 of a computer 48, the computer having associated with it the usual CRT monitor 50. Also associated with the computer 48 is a disk drive 52, and a printer 54 controlled by the computer 48. A main control unit 56 is provided, which is essentially a programmable timing unit which is adapted to control the solenoid valves 26, 28 and 36 in an appropriate sequence, and also to control the mixing motor 14 through a mixing rate control unit 58, the latter being adapted to control the rate and direction of mixing rotation of the spindle 16. Finally, the control unit 56 controls the converter 42 so that the latter sends discrete, time-separated signals to the computer 48. The control unit 56 is itself under the control of the computer 48.

The flow of mixed liquor and solids from the tank through the conduits 22 and 24 arises through means not shown, which means can include a pump. Alternatively, the flow can arise simply by connecting the conduits 22, 24 at locations of liquor flow in a wastewater treatment tank, such that the head at the two connections is different and results in liquid flow.

In its simplest form, the method provided herein for determining the oxygen uptake rate of bacteria in a body of liquid such as that in a wastewater treatment tank incorporates first withdrawing a sample of the liquid into the chamber defined by the container 10, where the probe 38 is located. This is accomplished by first closing the solenoid valve 26 and the solenoid valve 36, while leaving the valve 28 open. The inflowing material along the conduit 22, instead of flowing out of the base 20 along the conduit 24 will fill up the container 10 to the level of the conduit 30, along which it will flow out and down the standpipe 32, thence into the conduit 24 to return to the tank. When sufficient time has elapsed to allow the container 10 to become filled to the level of the conduit 30, the solenoid valve 28 is closed, and liquid flow through the container 10 ceases. With all three valves remaining closed, the mixing motor 14 is started, and the motor runs for a period of time sufficient to mix the contents thoroughly. The mixing motor is then stopped, and the air compressor 32 is turned on. The solenoid valve 36 is also opened to allow compressed air to be bubbled up to the chamber in the container 10 from the base 20. This proceeds for a period of time sufficient to allow complete aeration of the sample. Then, the air compressor 32 is stopped and the valve 36 is closed. The converter 42 continuously produces a digital signal corresponding to the analog signal being received by it from the probe 38, and passes this digital signal to the input 46 of the computer 48. The program in the computer 48 contains, as part of its data, information by which the computer can produce, for any such digital signal, a value for the dissolved oxygen content which corresponds. The computer samples the digital signal at timed intervals controlled by the program. There is thus generated a set of time-separated values for the dissolved oxygen content, which the computer program can display on the CRT monitor 50 or in printed form utilizing the printer 54. The values can also be stored on disk.

The computer program can be arranged to allow the printer to print out a graph showing the various dissolved oxygen values versus the corresponding times when the signal from the probe 38 is sampled.

The control unit 56 is programmed to retain each sample in the container 10 for a predetermined length of time, at the end of which the sample is emptied back into the tank, and a new sample is drawn. The emptying procedure involves opening both of the solenoid valves 26 and 28 simultaneously. Sufficient time is allowed to elapse for the contents of the container 10 to be emptied, and then the process is begun again.

Figure 2:
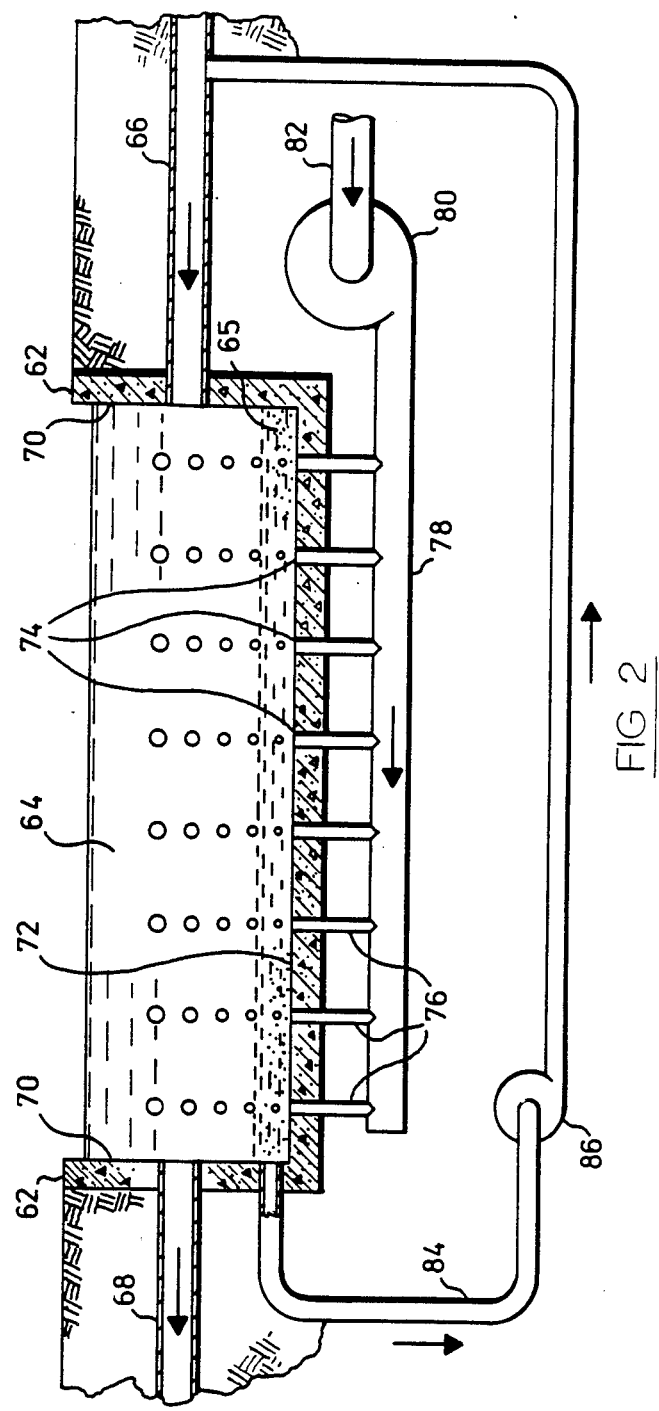
FIG. 2 is a vertical sectional view through an activated sludge wastewater treatment tank.
Figure 3A:
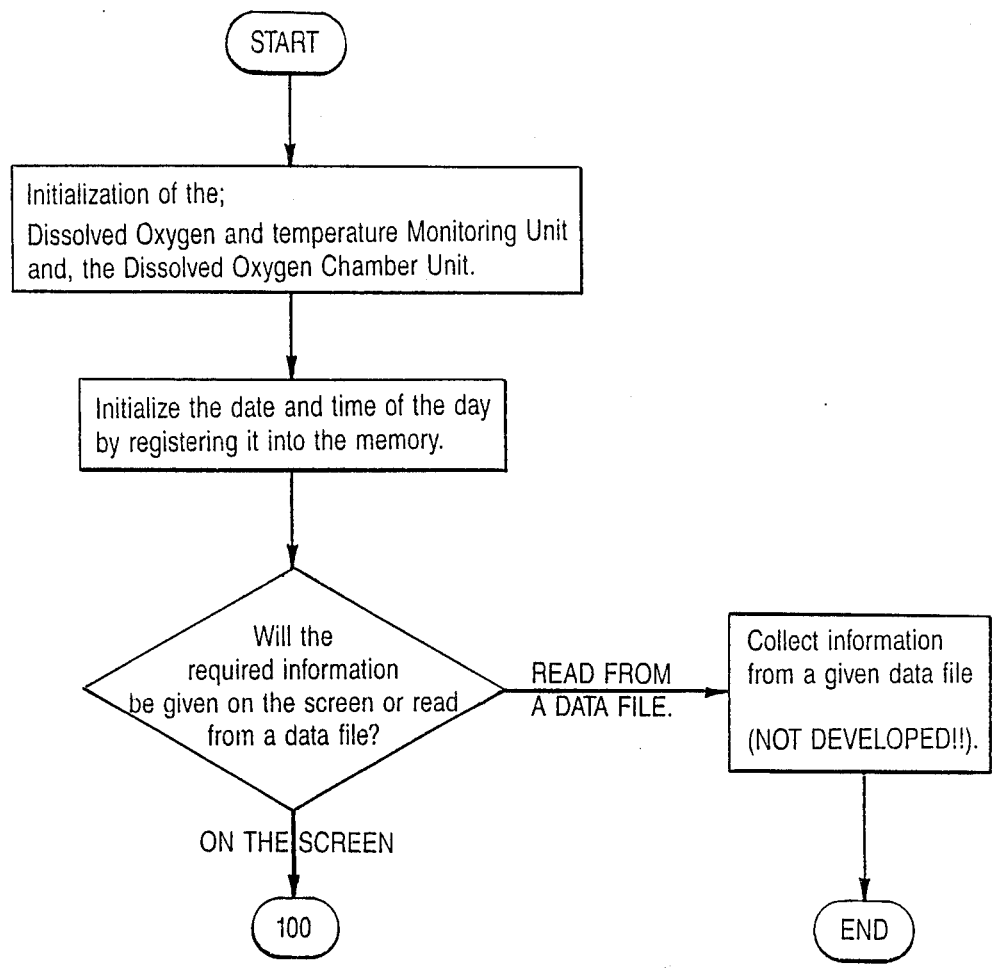
FIGS. 3a to 3h show a logic flow diagram of the operation program for the computer of FIG. 1.
Figure 3B:
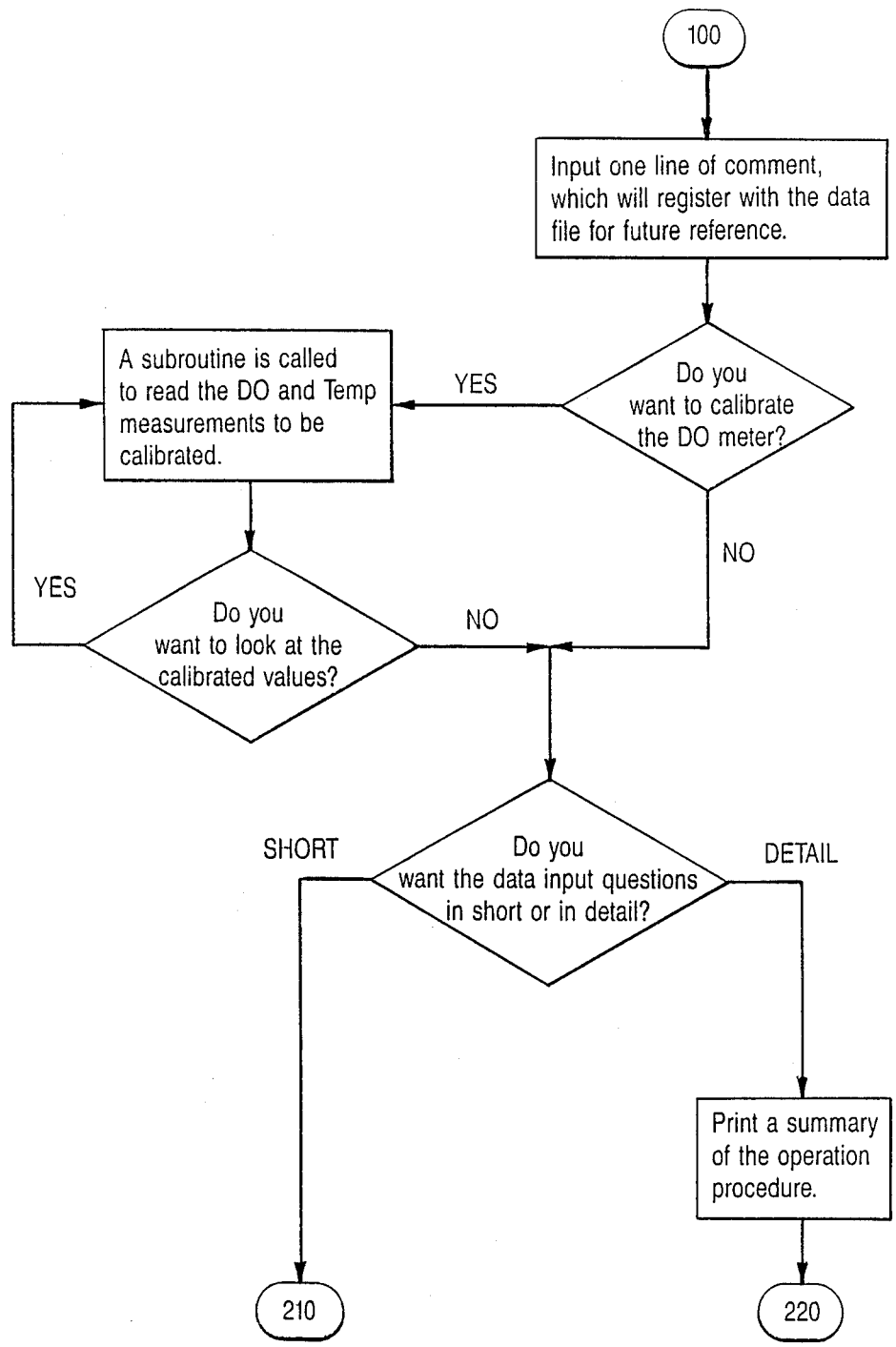
Figure 3C:
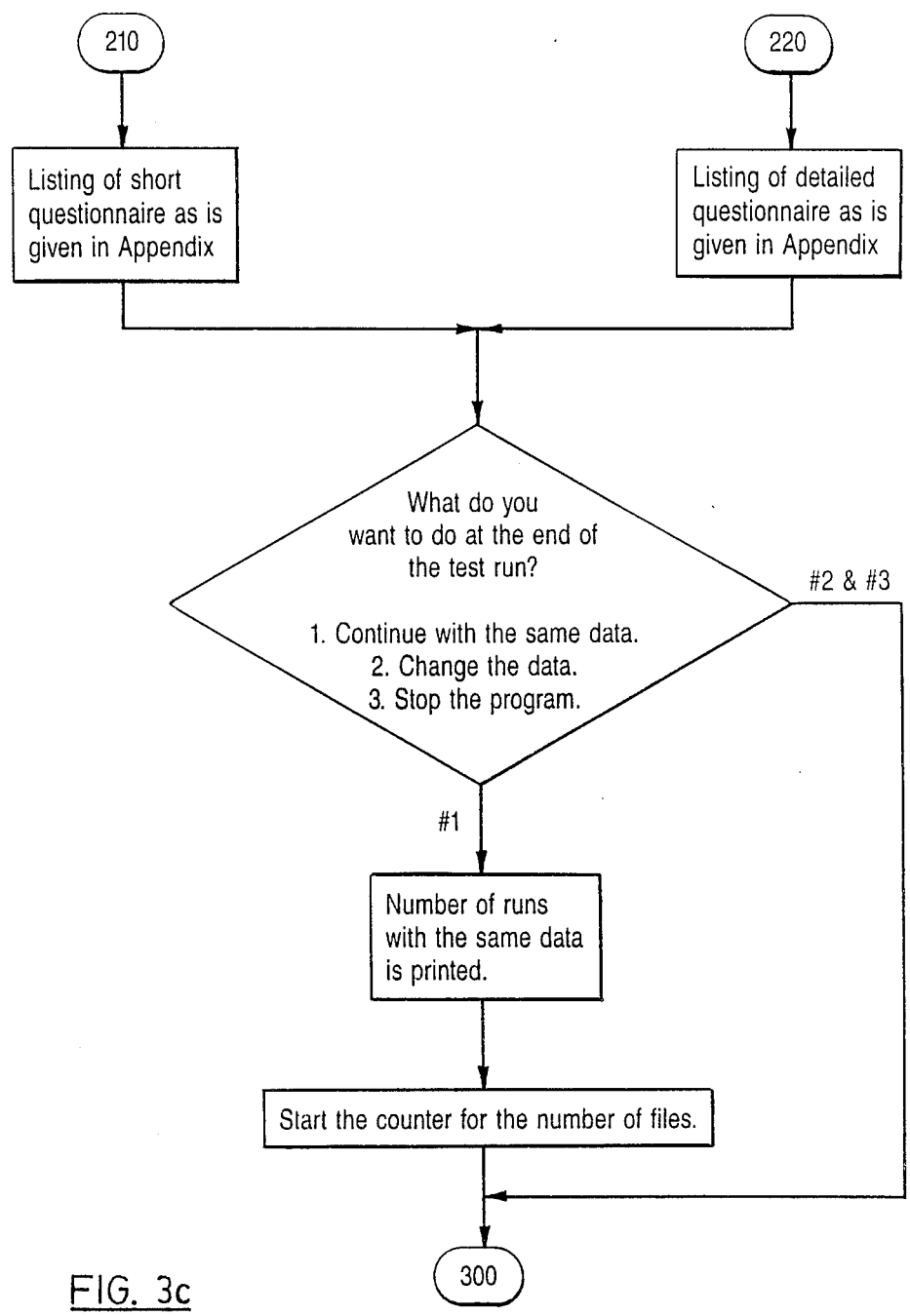
Figure 3D:
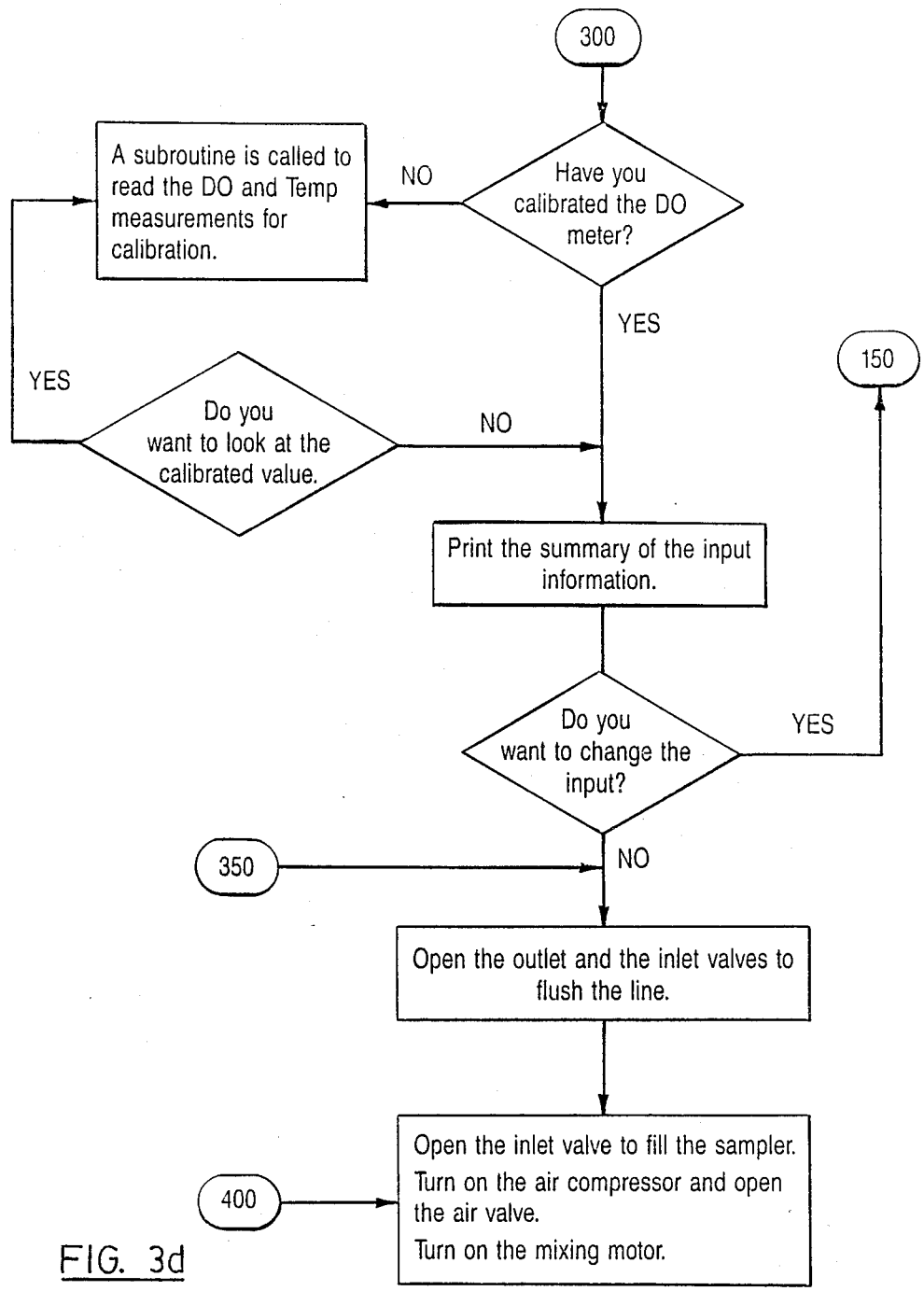
Figure 3E:
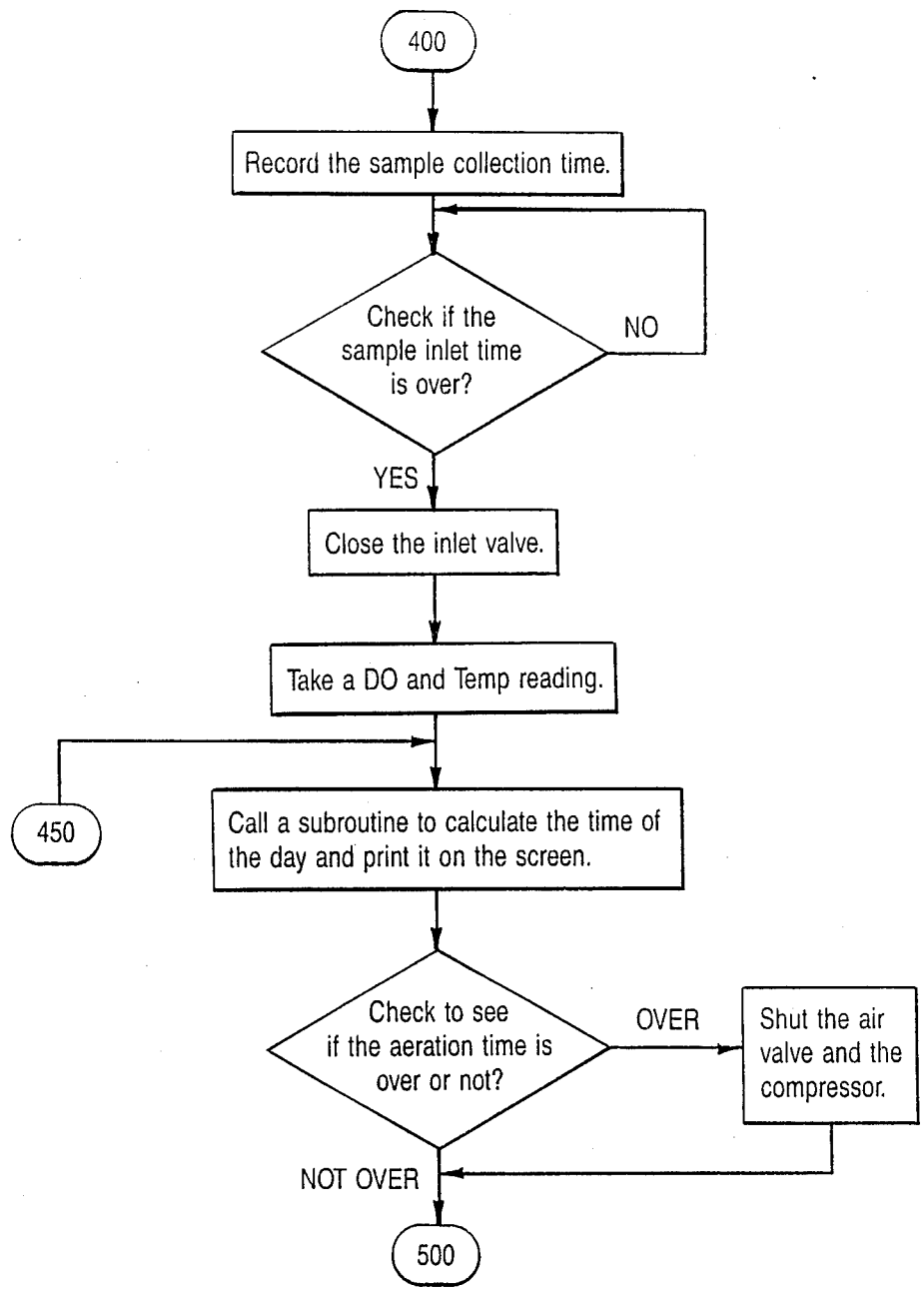
Figure 3F:
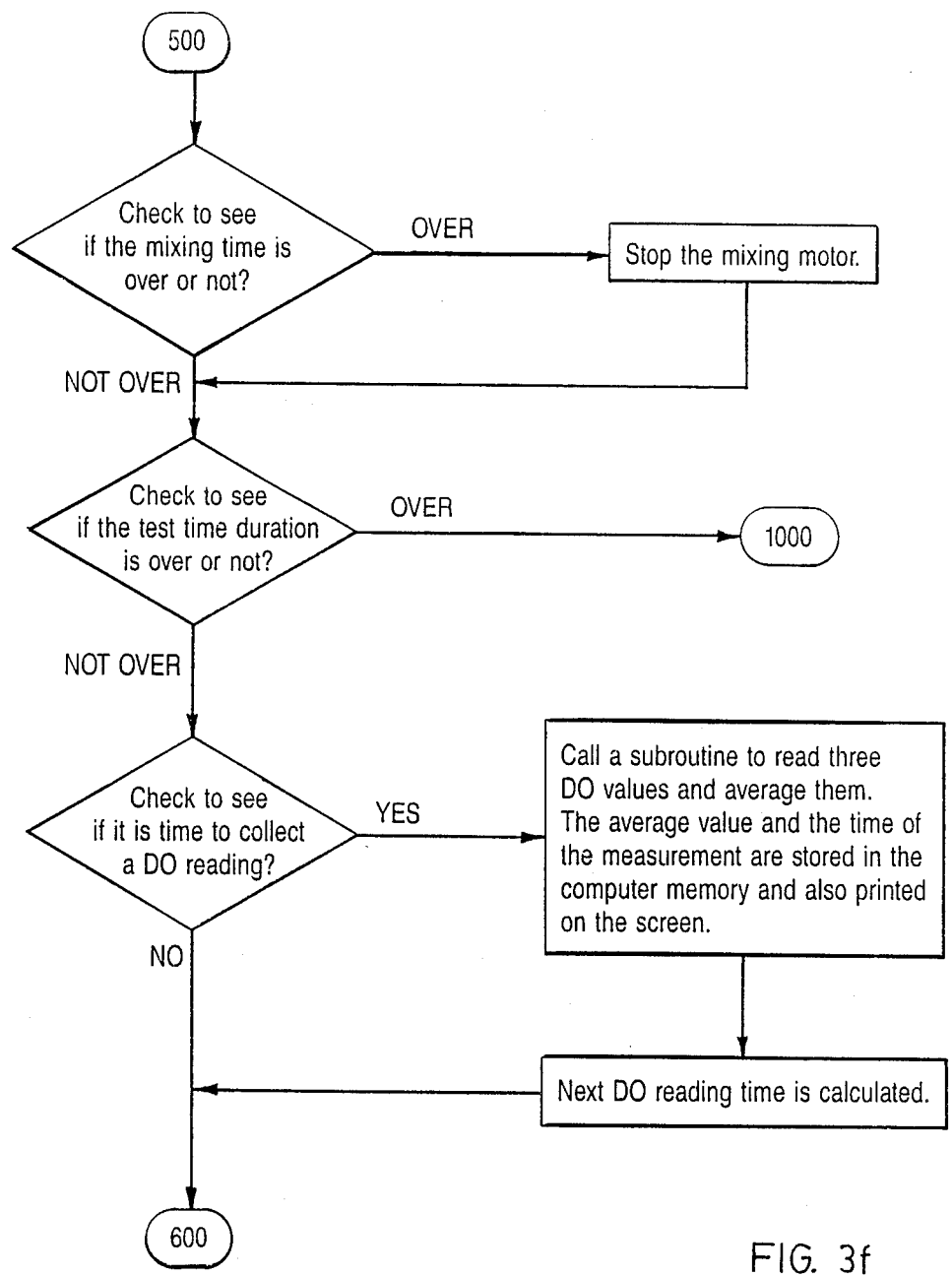
Figure 3G:
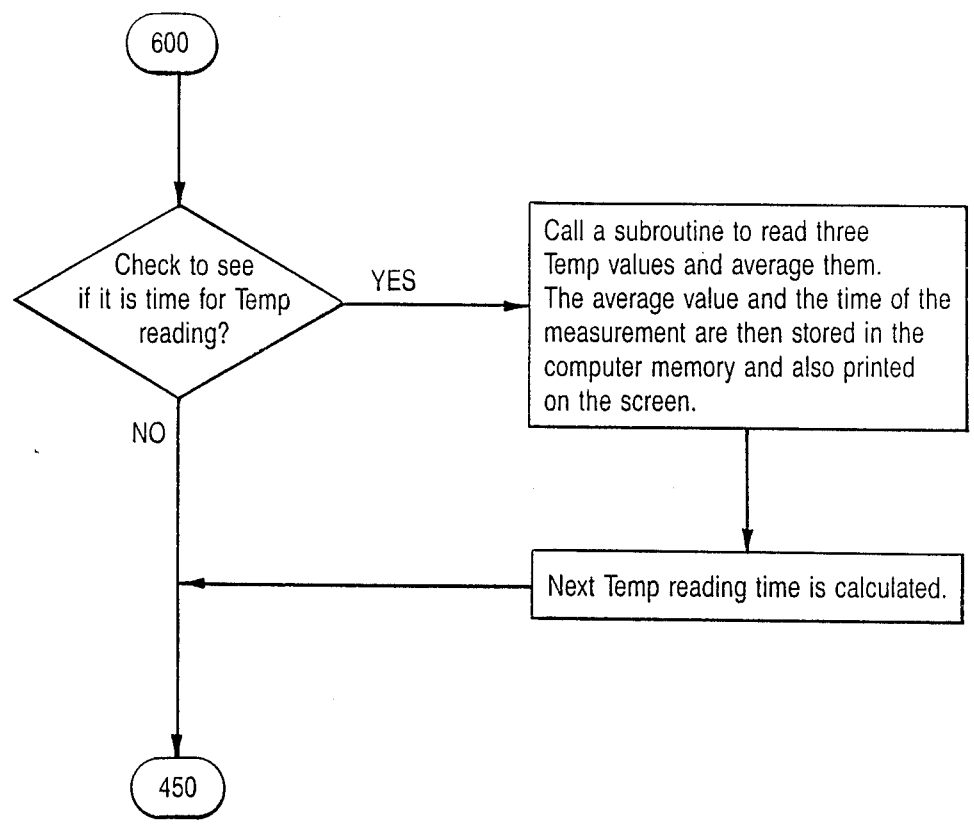
Figure 3H:
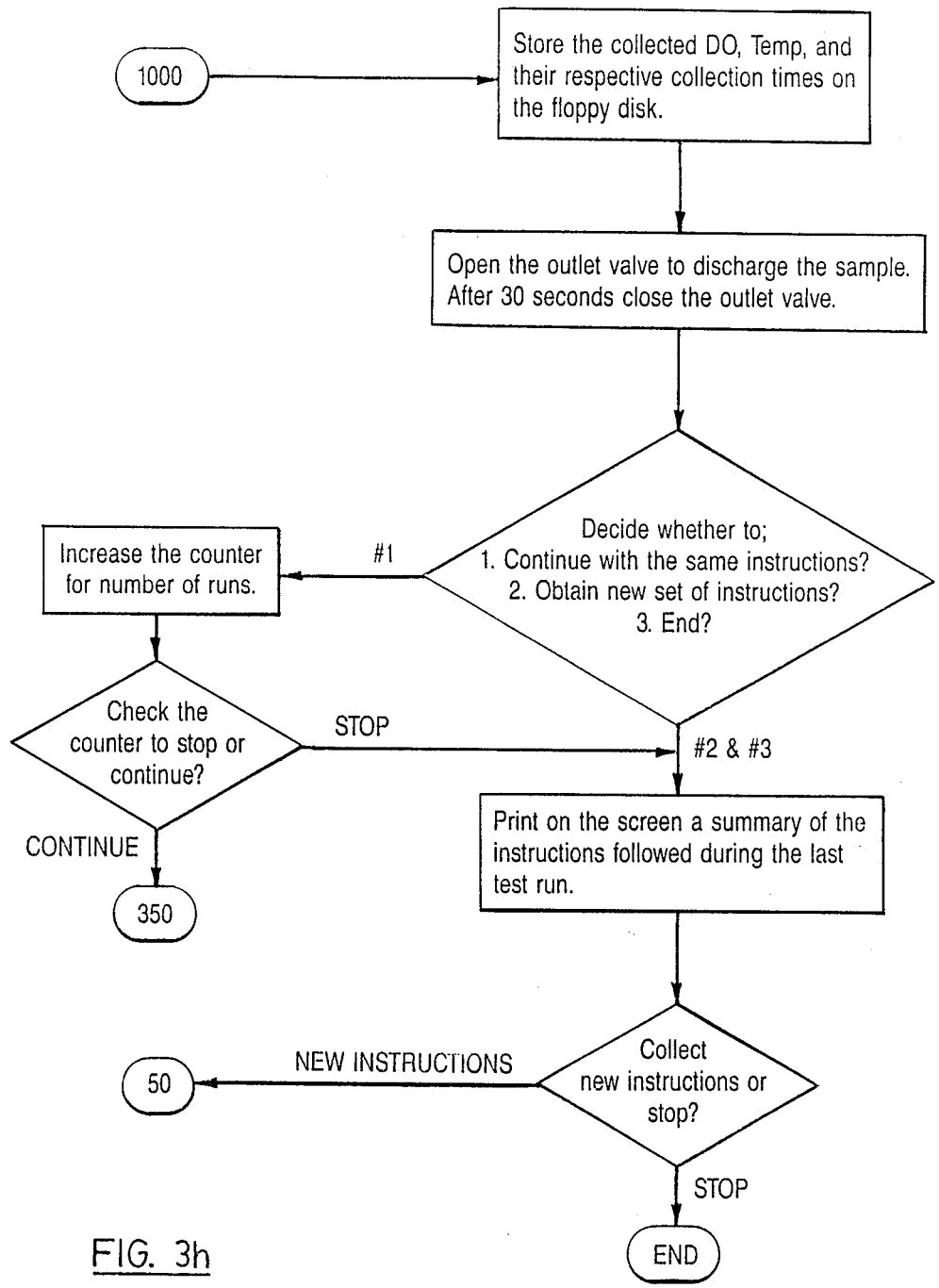
Figure 4A:
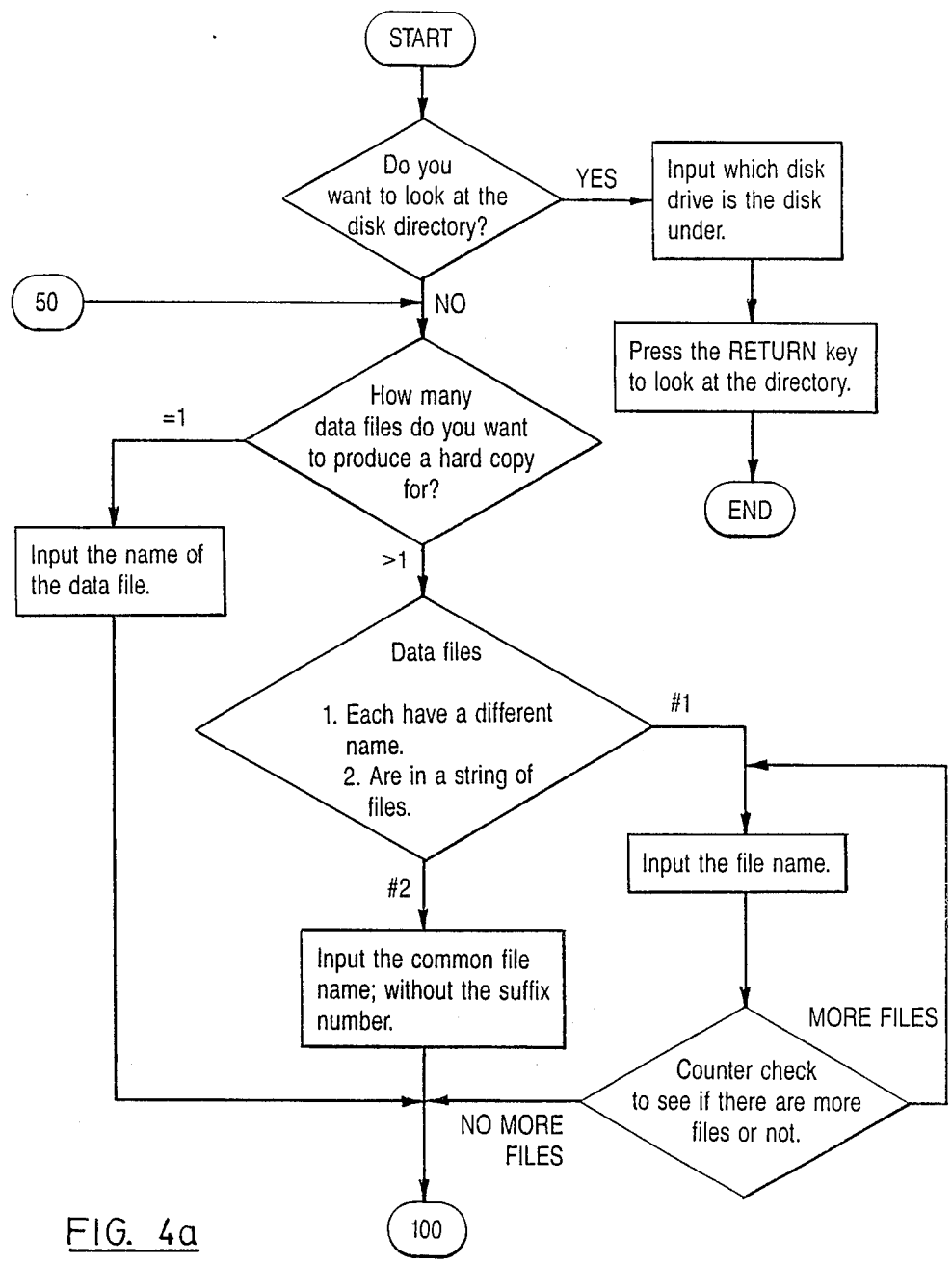
FIGS. 4a to 4f show the logic flow diagram for a detailed printout program.
Figure 4B:
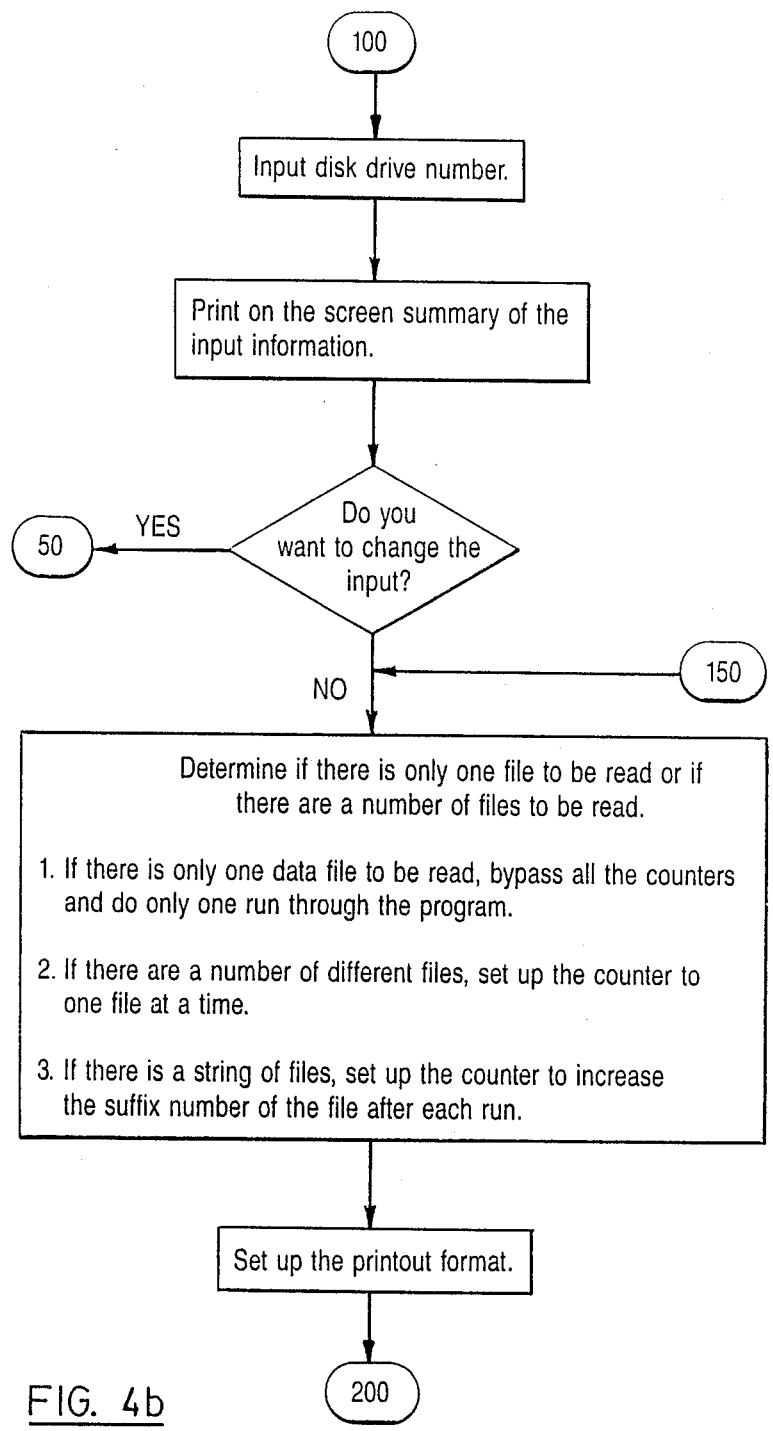
Figure 4C:
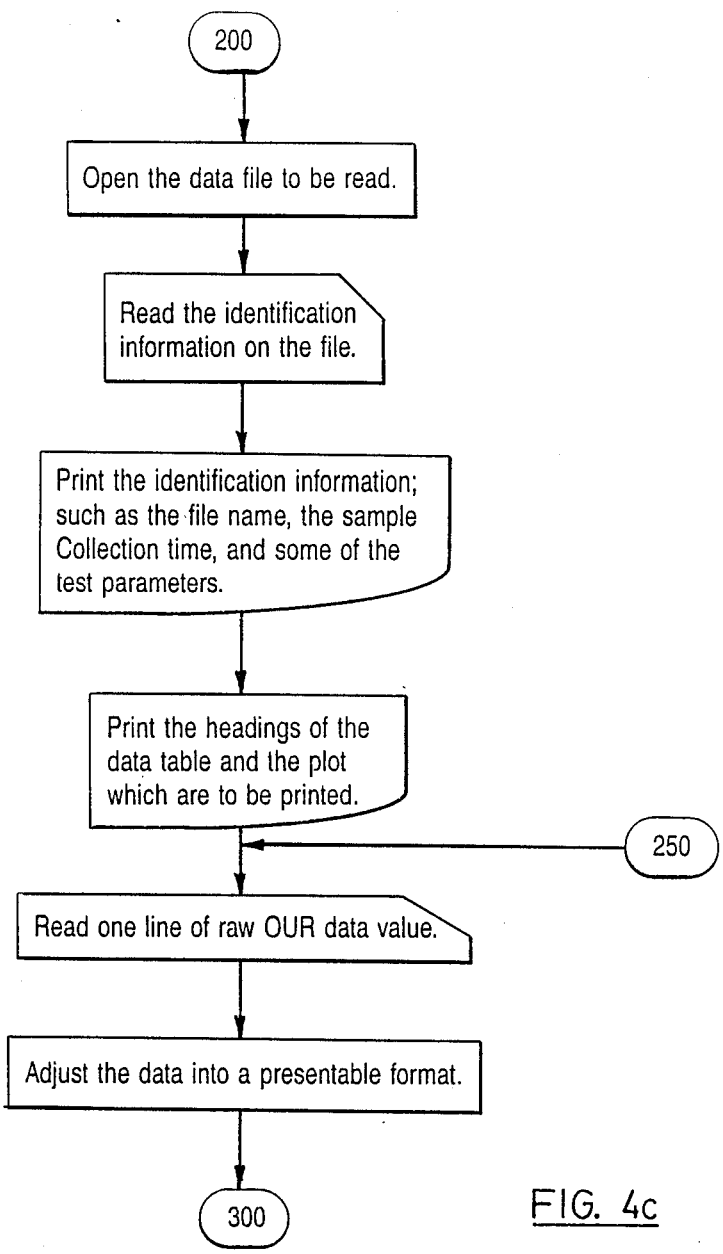
Figure 4D:
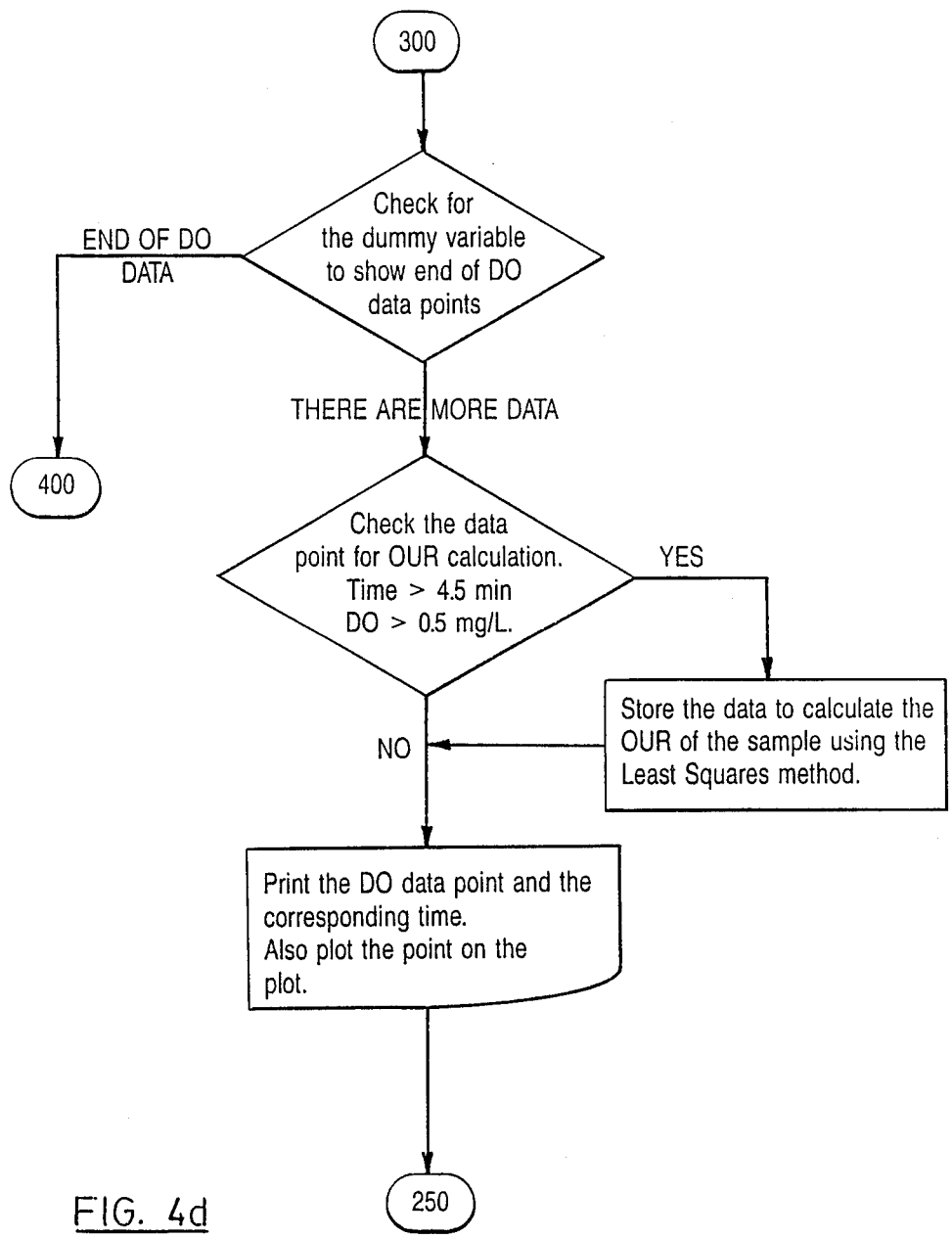
Figure 4E:
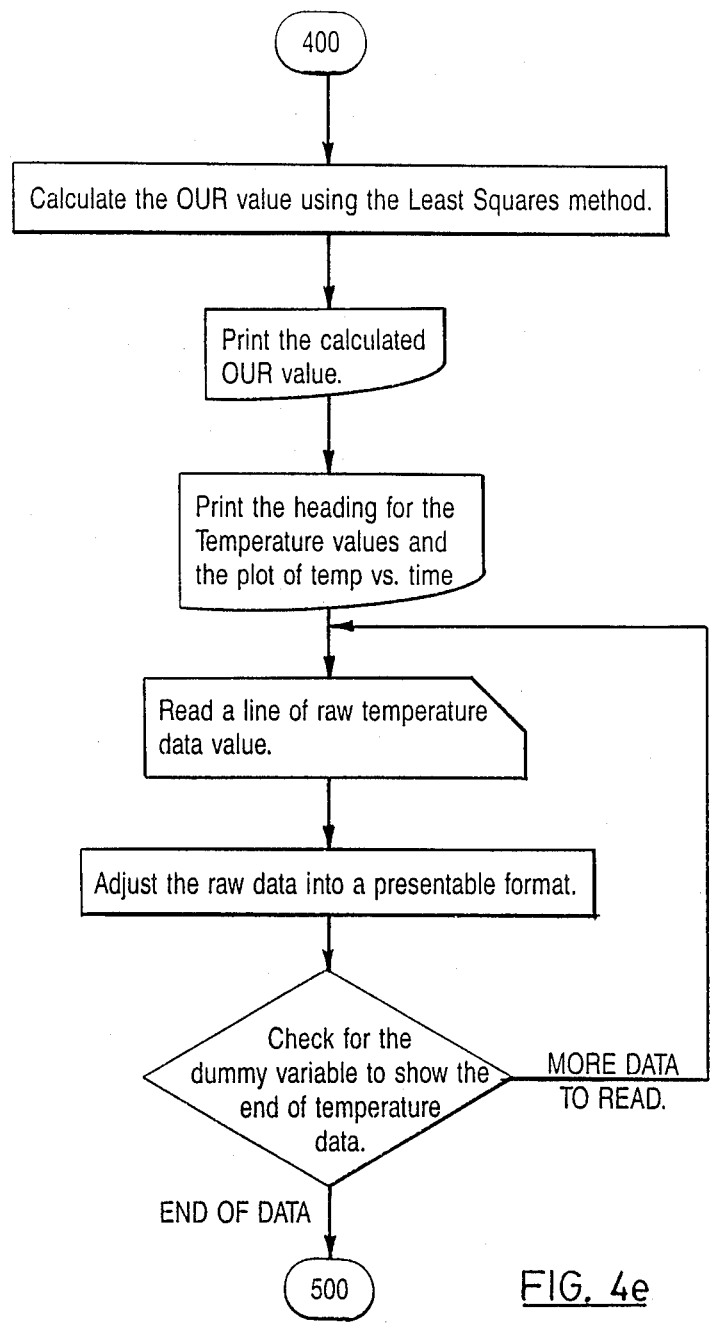
Figure 4F:
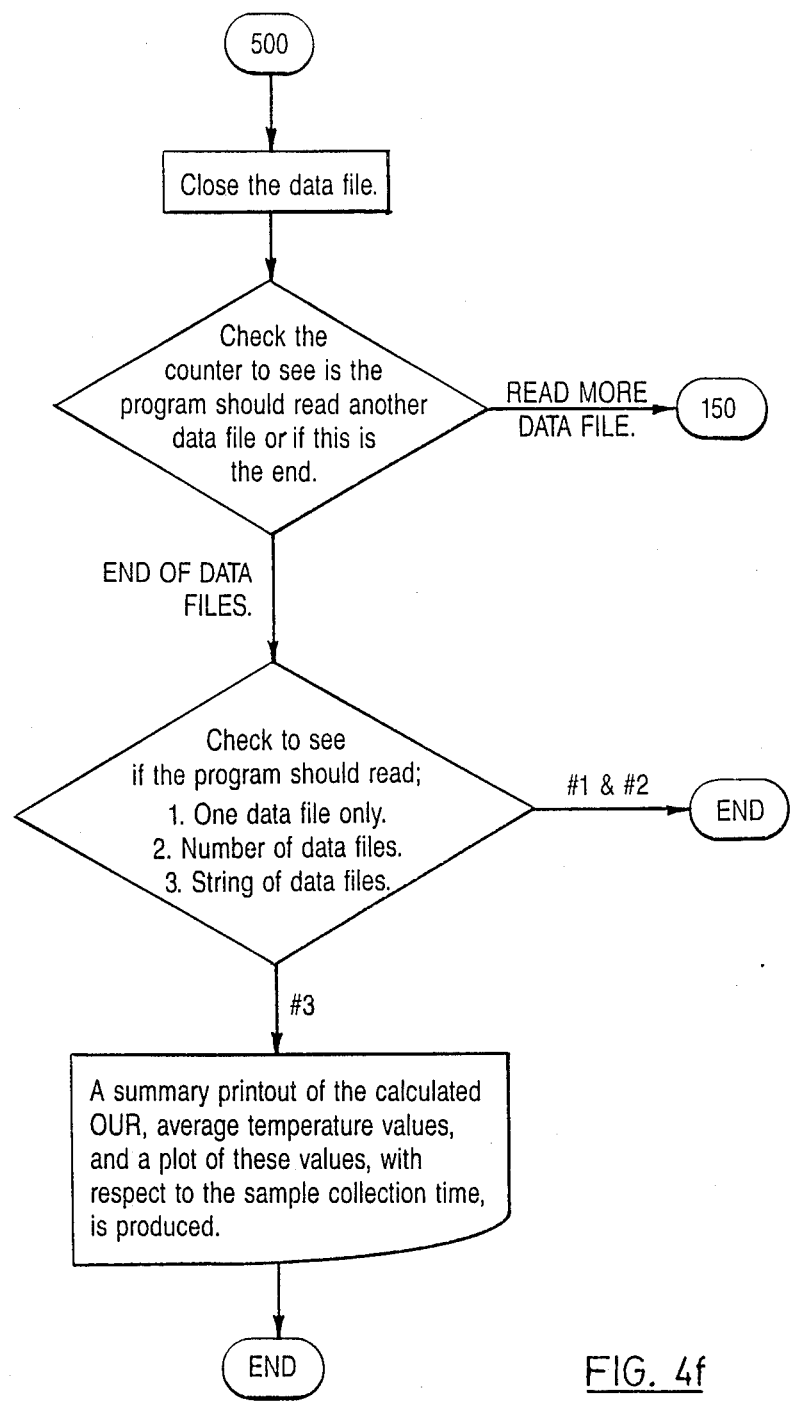
Figure 5A:
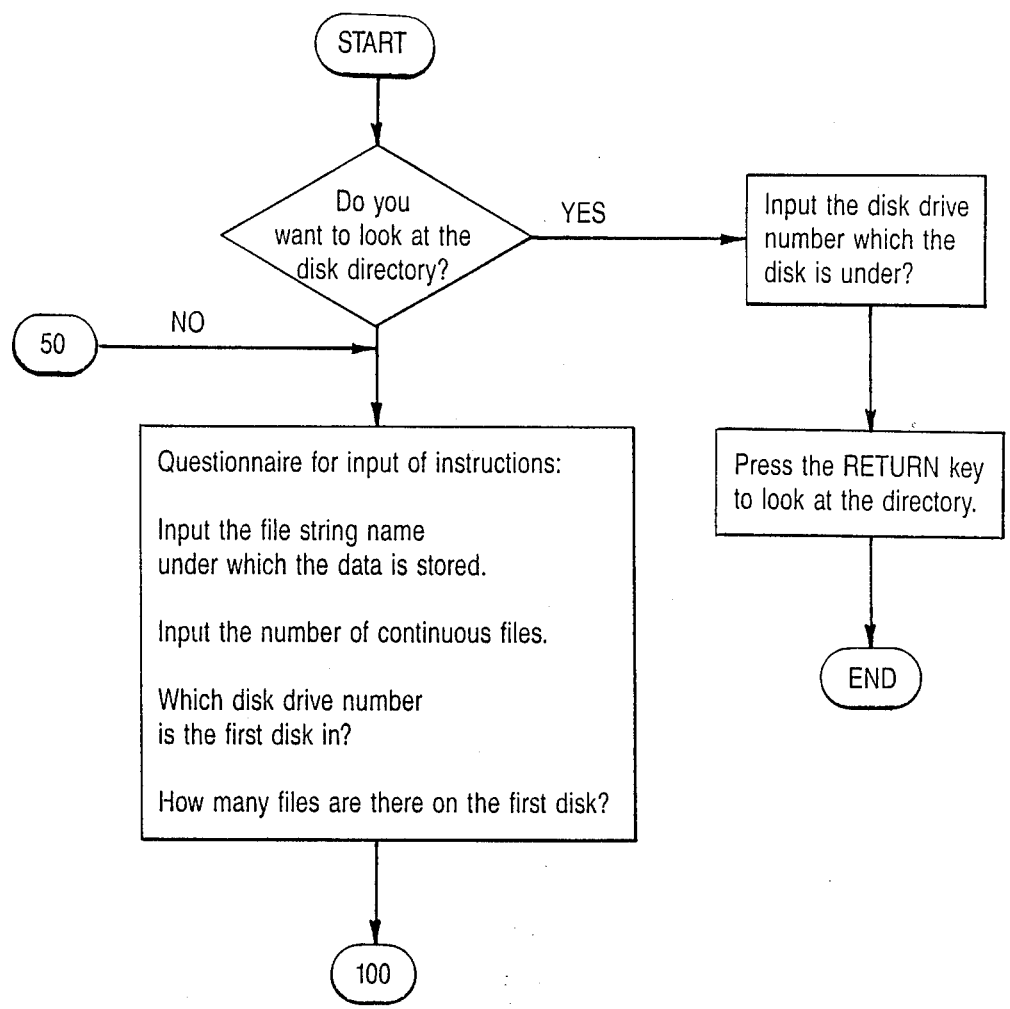
FIGS. 5a to 5e show a logic flow diagram for a summary printout program.
Figure 5B:
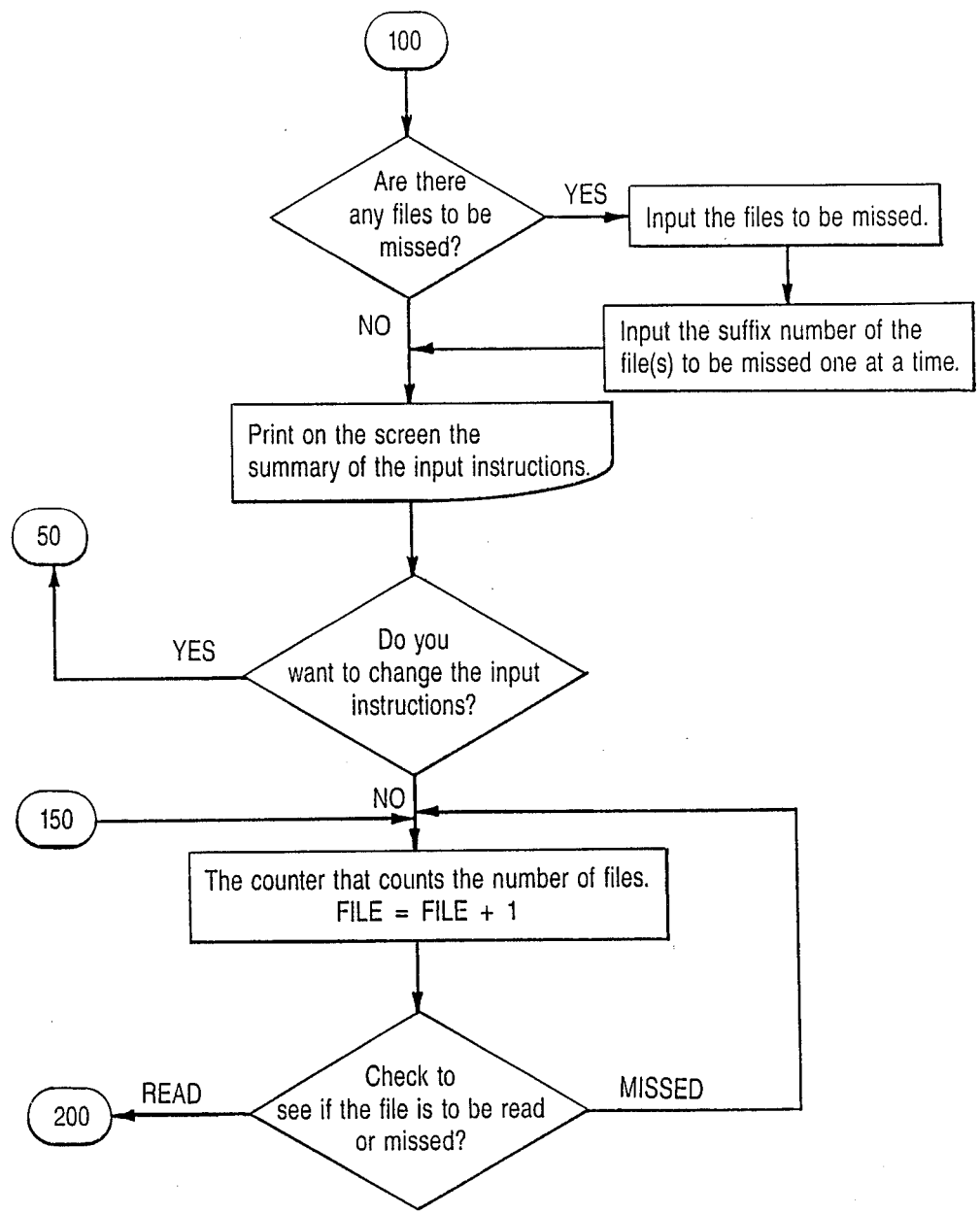
Figure 5C:
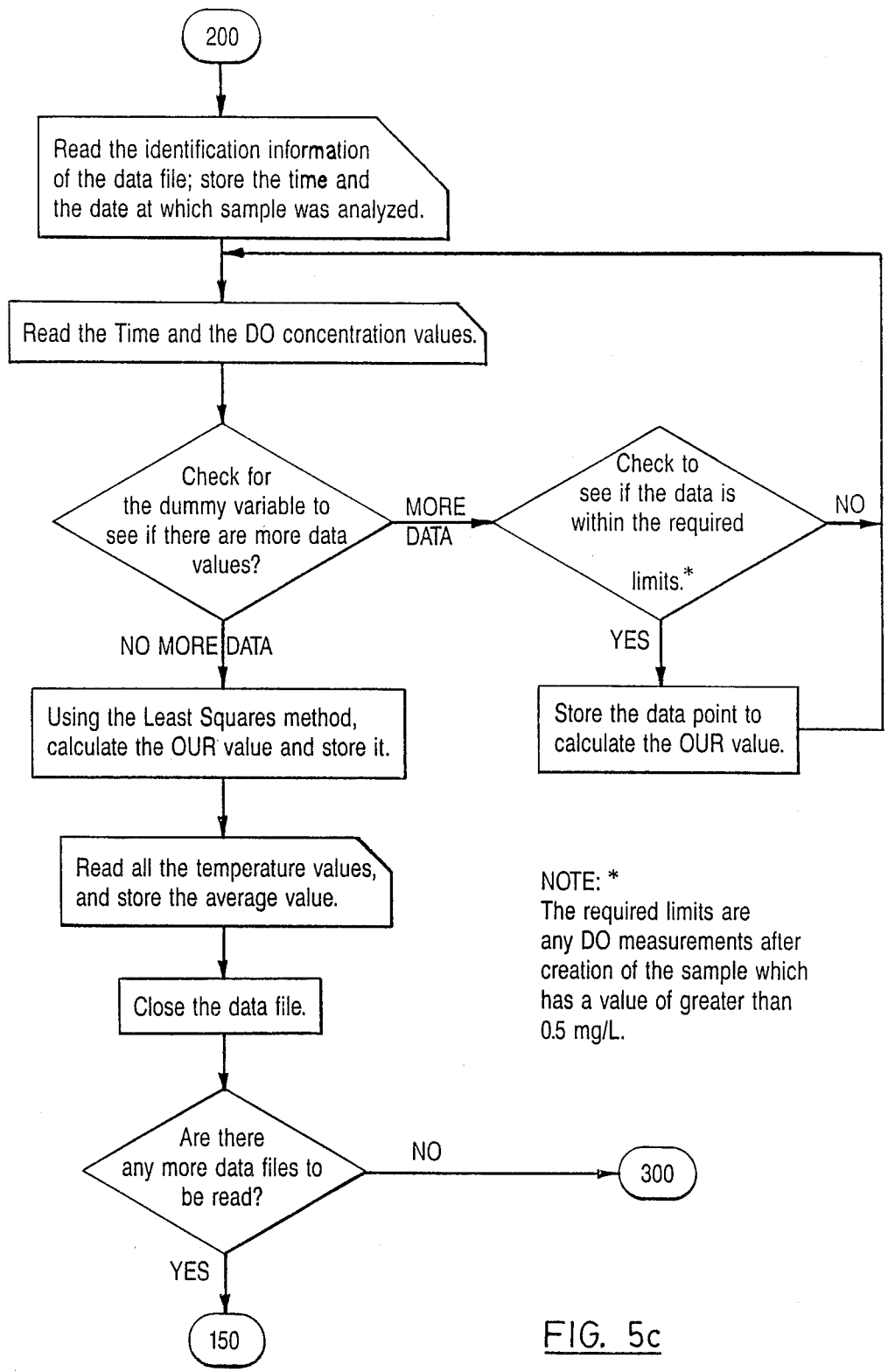
Figure 5D:
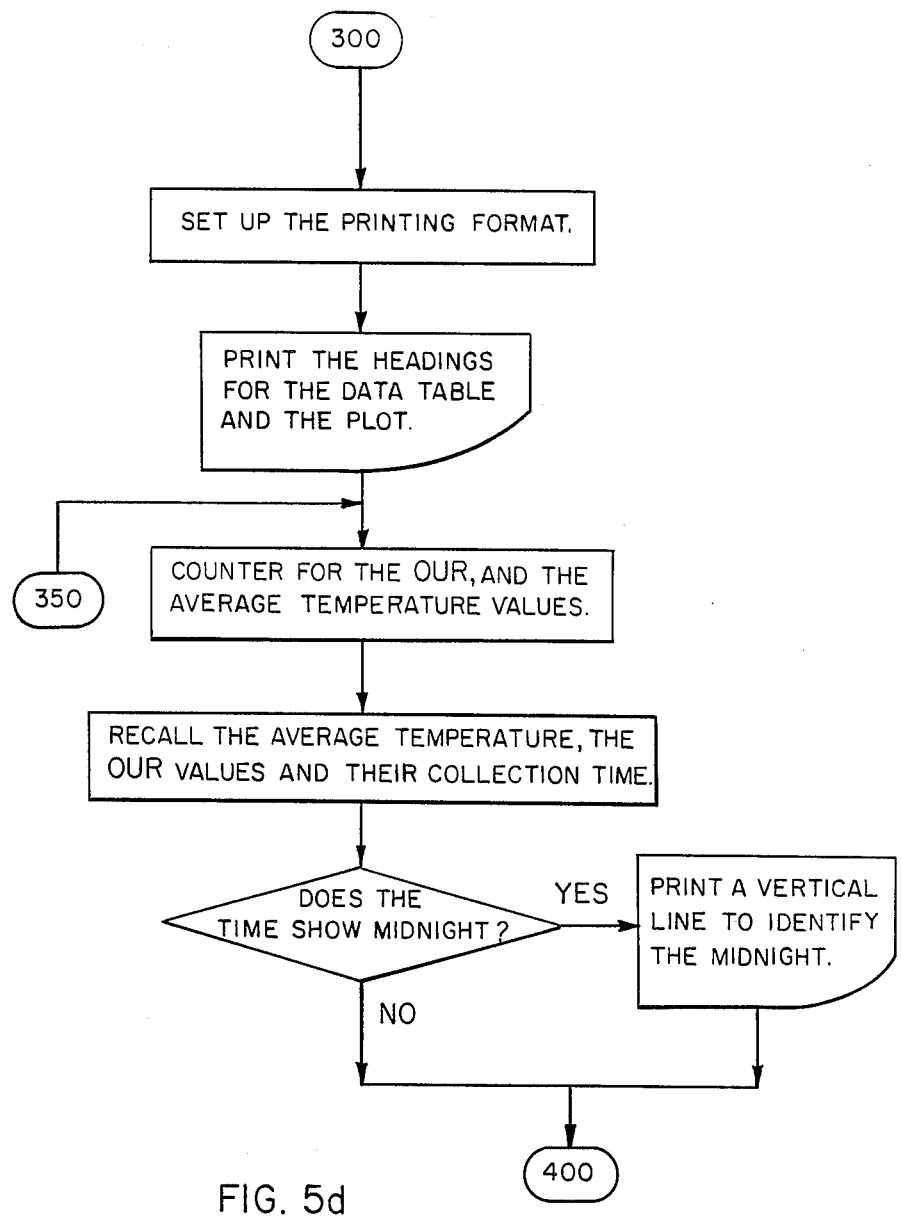
Figure 5E:
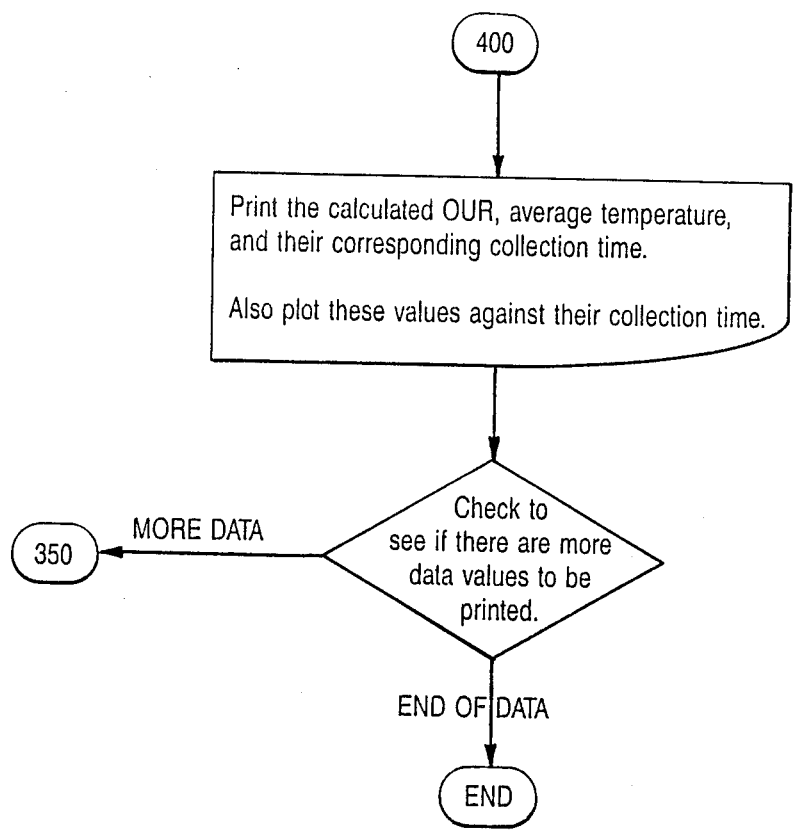

Attention is now directed to FIG. 2, which shows a vertical section through an activated sludge treatment tank 62 containing a liquid 64 and settled sludge 65, the tank 62 having an inlet pipe 66 and an outlet pipe 68. The tank 62 is defined by side walls 70 and a bottom wall 72. Through the bottom wall 72 extend a plurality of aeration nozzles 74, connected through short pipes 76 to a main plenum conduit 78 connected to the outlet of an air compressor 80 having an inlet conduit 82.

Also shown in FIG. 2 is a recycling pipe 84 connected between the downstream end of the tank 62 at the bottom and the inlet pipe 66, the pipe 84 having a pump 86 by which to promote flow in the pipe 84 in the direction toward the pipe 66.

An aspect of this invention is to control the compressor 80 or equivalent air moving means in such a way that, when the rate of decrease of the oxygen content in a given sample from the tank falls below a predetermined value, the aeration rate in the tank 62 can be decreased by either reducing the speed of the compressor 80, or shutting it down altogether for a predetermined period of time.

Naturally, the rate at which activated sludge can be removed from the tank 62 and returned to the inlet pipe 66 along the pipe 84 can also be governed in accordance with O.U.R. determined by the apparatus described above with respect to FIG. 1. Thus, whenever for any sample the determined O.U.R. is below a certain predetermined level, and the decreased O.U.R. does not appear to be due to a drop in incoming organics, the pump 86 can be turned on to recycle activated sludge to the upstream end of the tank 62.

FIGS. 3a to 3h show a logic flow chart for the program in the computer 48.

FIGS. 4a to 4f show a logic flow chart for a detailed printout program for the computer 48.

FIGS. 5a to 5e show a logic flow chart for a summary printout program for the computer 48.

It will thus be seen that there has been provided a convenient and fully automated process by which to accomplish a number of different desirable ends. In its simplest form, the apparatus described allows the oxygen uptake rate in an activated sludge wastewater treatment tank to be determined without any manual steps being required. In a more complex version, the O.U.R. can be determined on a regular basis by taking samples at timed intervals and determining the O.U.R. for each sample. This allows the operator to keep track of variations in the O.U.R. This information can then be utilized to maximize the efficiency of the overall plant by reducing the aeration rate in the tank when it is observed that the O.U.R. has significantly decreased. The reduction of the aeration rate can be done automatically by programming a predetermined level of O.U.R. in a sample, below which the aeration rate will be curtailed in some way. Finally, another use for the O.U.R. information is the control of the recycling of activated sludge from the downstream to the upstream end of a wastewater treatment tank. It will be understood that the latter procedure, whereby recycling is initiated upon fall of the O.U.R. below a predetermined level, may be appropriate only during daytime, when one would expect that the normally greater influx of organics would produce an increase rather than a decrease in the O.U.R.

While one embodiment of this invention has been illustrated in the accompanying drawings and described hereinabove, it will be evident to those skilled in the art that changes and modifications may be made therein, without departing from the essence of this invention, as set forth in the appended claims.

There follows three program listings written in computer basic. The first program is the operational procedure and corresponds to the logic flow diagram of FIGS. 3a–3g. The second printout is that of a detailed printout program corresponding to the logic flow diagram of FIGS. 4a–4f. The third listing is for a summary printout program corresponding to the logic flow diagram of FIGS. 5a–5e.

```
1390 PRINT#7,"              STARTING   ",D1$,",",M1$,",",Y1$," AT ",ST$,1
1400 PRINT#7,"              FROM DATA FILE ==== ",QNN$," 1  THROUGH    ",NZ
1410 PRINT#7,"              "
1420 PRINT#7,"              """
1430 PRINT#7,"
1440 PRINT#7,"COMMENT ";COM$
1450 PRINT#7,"
1460 PRINT#7,"                                               """
1470 PRINT#7," TIME     OUR     TEMP"
1480 PRINT#7,"OF DAY  MG/L.HR   C "
1490 PRINT#7,TAB(20)" 06    10    14    18    22    26    30    34    38"
1500 PRINT#6,CHR$(1)
1510 PRINT#7,TAB(65)" 42    46    50      "
1520 PRINT#6,CHR$(24)
1530 PRINT#7,"————————————————————————"
1540 PRINT#6,CHR$(1)
1550 PRINT#7,TAB(20)"++————+————+————+————+————+————+OUR+MG/L.HR+————+————+————"
1560 PRINT#7,TAB(75)"————"
1570 PRINT#6,CHR$(24)
1580 FOR OX=1 TO NZ
1590 W2=(SH(OX)-6)*(2.5/2)
1600 IF W2<0 THEN W2=0
1610 W3=(AVT(OX)-12)*5
1620 IF W3<0 THEN W3=0
1630 NS=VAL(LEFT$(ST$(OX),2))
1640 IF NS<OS THEN GOSUB 1760
1650 OS=NS
1660 PRINT#7,ST$(OX)
1670 PRINT#6,CHR$(1)
1680 PRINT#1,SH(OX),AVT(OX)
1690 PRINT#7,TAB(20)"|"TAB(W2)"+"
1700 PRINT#7,TAB(20)"|"TAB(W3)"."
1710 PRINT#6,CHR$(24)
1720 NEXT OX
1730 CLOSE 6
1740 CLOSE 7:CLOSE 1
1750 END
1760 PRINT#6,CHR$(24)
1770 PRINT#7,"————————————————————————"
1780 PRINT#6,CHR$(1)
1790 PRINT#7,TAB(20)"++————+————+————+————+————+————+OUR+MG/L.HR+————+————+————+"
1800 PRINT#7,TAB(75)"————"
1810 PRINT#6,CHR$(1)
1820 RETURN
730 DX=0:INPUT#5,DOM$
740 DX=DX+1:DX$=STR$(DX)
750 REM TO CONT
760 PRINT"READING FILE",NN$
770 INPUT#15,EN$,EM$:IF EN$<>"00" GOTO990
780 OD=0:TS=0:CU=0:CX=0:CY=0:SX=0:NP=0
790 FOR ZX=1 TO 100
800 INPUT#5,TDO$
810 IF LEN(TDO$)<7 GOTO 970
820 LN=LEN(TDO$)
830 LN=LN-8
840 T$=LEFT$(TDO$,LN)
850 DO$=RIGHT$(TDO$,8)
860 TW$=RIGHT$(T$,LN-2):TS=VAL(TW$)
870 T=(INT((VAL(TW$)/60)*100))/100
880 OD=VAL(DO$)
890 IF TS<270 THEN NEXT ZX
900 IF OD<0.50 THEN NEXT ZX
910 NP=NP+1
920 CU=(OD*TS)+CU
930 CX=(TS+CX)
940 CY=(OD+CY)
950 SX=(TS*TS)+SX
960 NEXT ZX
970 LS=((NP*CU)-(CX*CY))/((NP*SX)-(CX*CX))
980 XM=(INT(LS*60000))/1000
990 XH=XM*60*(1-2)
1000 TX=0:INPUT#5,DOM$
1010 TX=TX+1:TX$=STR$(TX)
1020 ATE=0:TE=0
1030 REM TO CONT
1040 FOR ZX=1 TO 50
```

```
1050 INPUT#5,TTE$
1060 IF LEN(TTE$)<8 GOTO 1170
1070 LN=LEN(TTE$)
1080 LN=LN-7
1090 T$=LEFT$(TTE$,LN)
1100 TE$=RIGHT$(TTE$,7)
1110 TW$=RIGHT$(T$,LN-2):TS=VAL(TW$)
1120 T=(INT((VAL(TW$)/60)*100))/100
1130 TE=(INT((((VAL(TE$)/800)/0.0429)-5)*10))/10
1140 WO=INT((TE-10)*2.5)+24
1150 ATE=TE+ATE
1160 NEXT ZX
1170 AVT=ATE/(ZX-1)
1180 CLOSE 5,8,5
1190 CLOSE 15,8,15
1200 SH(VX)=XH
1210 ST$(VX)=H$+" "+MT$
1220 AVT=(INT(AVT*10))/10
1230 AVT(VX)=AVT
1240 NEXT VX
1250 OPEN 7,4
1260 OPEN 6,4,6:CMD6
1270 OPEN 2,4,2:PRINT#2,TAB(8)"99.99"TAB(8)"99.9":CLOSE2
1280 OPEN 1,4,1
1290 PRINT#6,CHR$(24)
1300 PRINT#7,"."
1310 PRINT#7,"."
1320 PRINT#7,"
1330 PRINT#7,"        "
1340 PRINT#7,"       "
1350 PRINT#7,"
1360 PRINT#7,"              SUMMARY OF THE DATA COLLECTE"
1370 PRINT#7,"
1380 PRINT#7,"
READY.

100 REM****************************
110 REM
120 REM     PRINTOUT PROGRAM
130 REM        TO DO A STATISTICAL ANALYSIS ON THE DATA
140 REM        CALCULATE THE OUR PER HOUR AND
150 REM        PRINTOUT THE SUMMARY OF THE RESULTS.
160 REM
170 REM     PROGRAME BY: BIJAN AIDUN
180 REM     DATE       : MAY,06,1985
190 REM****************************
200 DIM ZNN$(600):DIM SH(600):DIM ST$(600):DIM AVT(600)
210 PRINT"_____DO YOU WANT TO LOOK AT "
220 INPUT"THE DISK DIRECTORY Y/N";YN$
230 IF ASC(YN$)=78 GOTO 280
240 IF ASC(YN$)<>89 GOTO 210
250 INPUT"__WHICH DISK DRIVE #";DD$
260 PRINT"_____$"+DD$
270 PRINT"_HIT RETURN KEY.":PRINT"_":END
280 PRINT"_____UNDER WHAT FILE STRING NAME IS"
290 INPUT"_THE DATA STORED ";QNN$
300 NN$=QNN$
310 PRINT"_____HOW MANY CONTINUOUS RUNS"
320 INPUT"_DO YOU WANT THE DATA FOR";NZ
330 INPUT"___WHICH DISK DRIVE IS THE DATA DISK IN";DD$
340 PRINT"___NOTE THE FIRST DISK"
350 PRINT"HAS TO BE UNDER DRIVE #0"
360 PRINT"___HOW MANY FILES ARE"
370 INPUT"_THERE ON THE FIRST DISK";XT
380 PRINT"_____THE GIVEN INFORMATION IS AS SUCH"
390 PRINT"_**DATA IS STORED UNDER , ";NN$
400 PRINT"_**THERE WILL BE ";NZ;" DATA FILES READ"
410 PRINT"_**THE DISK IS IN DRIVE #  ";DD$
420 PRINT"_**THERE ARE ";XT;" FILES ON THE FIRST DISK"
430 INPUT"__DO YOU WANT TO CHANGE, Y/N";Y$
440 IF ASC(Y$)=89 THEN PRINT"_":GOTO 280
450 IF ASC(Y$)<>78 GOTO 430
460 REM****************************
470 REM
```

```
480 REM     START OF PROGRAM TO
490 REM     READ & PRINTOUT DATA
500 REM***********************************
510 FOR VX=1 TO NZ
520 IF VX=(XT+1)    THEN DD$="1"
530 IF VX=(XT+141)  THEN DD$="0"
540 IF VX=(XT+281)  THEN DD$="1"
550 IF VX=(XT+421)  THEN DD$="0"
560 IF VX=(XT+561)  THEN DD$="1"
570 IF VX=(XT+701)  THEN DD$="0"
580 IF VX=(XT+841)  THEN DD$="1"
590 QZ=QZ+1
600 QZ$=STR$(QZ)
610 NN$=QNN$+QZ$
620 OPEN 15,8,15
630 OPEN 5,8,5,DD$+":"+NN$+",S,R"
640 INPUT#5,DMY$:INPUT#5,HMS$
650 INPUT#5,TT$:INPUT#5,AT$
660 INPUT#5,MX$:INPUT#5,DR$:INPUT#5,TEMPI$:INPUT#5,COM$
670 DMY$=RIGHT$(DMY$,6)
680 D$=LEFT$(DMY$,2):MY$=RIGHT$(DMY$,4):M$=LEFT$(MY$,2):Y$=RIGHT$(DMY$,2)
690 HR$=RIGHT$(HMS$,6):H$=LEFT$(HR$,2):MS$=RIGHT$(HMS$,4)
700 MT$=LEFT$(MS$,2):S$=RIGHT$(HMS$,2):TEMPI$=RIGHT$(TEMPI$,3)
710 TT$=RIGHT$(TT$,3):AT$=RIGHT$(AT$,3):MX$=RIGHT$(MX$,3):DR$=RIGHT$(DR$,3)
720 IF VX=1 THEN D1$=D$:M1$=M$:Y1$=Y$
2710 PRINT#7,"——          ————"
2720 PRINT#6,CHR$(1)
2730 PRINT#7,TAB(20)"++——+——+——+——+——+——+OUR+MG/L.HR—+——+——+——+"
2740 PRINT#7,TAB(75)"———"
2750 PRINT#6,CHR$(1)
2760 RETURN
READY.

READY.
$0$0
2050 PRINT#7,TAB(15)"****************** FOR THE FILE. ";NN$
2060 PRINT#7,"  "
2070 CLOSE 15,8,15
2080 PRINT"********** END OF DATA ********"
2090 PRINT"******* FOR FILE;";NN$
2100 PRINT#6,CHR$(0)
2110 FOR R=1 TO 3
2120 PRINT#7,"                              "
2130 NEXT R
2140 PRINT#6,CHR$(24)
2150 CLOSE 7,4
2160 CLOSE 2,4,2
2170 CLOSE 1,4,1
2180 CLOSE 6,4,6
2190 IF NZ=1 THEN END
2200 SH(VX)=XH
2210 ST$(VX)=H$+":"+MT$
2220 NEXT VX
2230 IF DZ=1 THEN END
2240 OPEN 7,4
2250 OPEN 6,4,6:CMD6
2260 PRINT#6,CHR$(48)
2270 PRINT#7,"                              "
2280 PRINT#7,"                              "
2290 PRINT#7,"                              "
2300 PRINT#7,"                              "
2310 PRINT#7,"    "
2320 PRINT#7,"    "
2330 PRINT#7,"           SUMMARY OF THE DATA COLLECTED "
2340 PRINT#7,"           ———————————————"
2350 PRINT#7," "
2360 PRINT#7,"      STARTING FROM ";D1$;"/";M1$;"/";Y1$;"  AT ";ST$(1)
2370 PRINT#7,"      FROM DATA FILE  ═══ ";QNN$;" 1 THROUGH ";NZ
2380 PRINT#7,"      ————————————————————————"
2390 PRINT#7,"                              "
2400 PRINT#7,"                              "
2410 PRINT#7,"COMMENT";COM$
2420 PRINT#7,"                              "
```

```
2430 PRINT#7,"
2440 PRINT#7," TIME         OUR"
2450 PRINT#7,"OF DAY     MG/L.HR"
2460 PRINT#7,TAB(20)" 17   18   19   20   21   22   23   24   25"
2470 PRINT#6,CHR$(1)
2480 PRINT#7,TAB(65)" 26   27   28   "
2490 PRINT#6,CHR$(24)
2500 PRINT#7,"━━━━━━━━━━━━━━━━━━━━"
2510 PRINT#6,CHR$(1)
2520 PRINT#7,TAB(20)"++----+----+----+----+----+----+OUR+MG/L.HR-+----+----+----+"
2530 PRINT#7,TAB(75)"----"
2540 PRINT#6,CHR$(24)
2550 FOR OX=1 TO NZ
2560 W2=(SH(OX)-17)*5
2570 IF W2<0 THEN W2=0
2580 IF NZ<50 GOTO 2620
2590 NS=VAL(LEFT$(ST$(OX),2))
2600 IF NS<OS THEN GOSUB 2700
2610 OS=NS
2620 PRINT#7,ST$(OX);"        ";SH(OX)
2630 PRINT#6,CHR$(1)
2640 PRINT#7,TAB(20)"I"TAB(W2)"+"
2650 PRINT#6,CHR$(24)
2660 NEXT OX
2670 CLOSE 6
2680 CLOSE 7
2690 END
2700 PRINT#6,CHR$(24)
1390 DO$=RIGHT$(TDO$,8)
1400 TW$=RIGHT$(T$,LN-2):TS=VAL(TW$)
1410 T=(INT((VAL(TW$)/60)*100))/100
1420 OD=VAL(DO$)
1430 WO=INT(OD*5)+24
1440 PRINT#1,TS,T,OD
1450 PRINT#6,CHR$(1)
1460 IF ZX=10 THEN S1X=TS:S3Y=OD:PRINT#7,TAB(WO+1)"●"
1470 IF ZX=26 THEN S2X=TS:S4Y=OD:PRINT#7,TAB(WO+1)"●"
1480 PRINT#7,TAB(24)"I"TAB(WO-24)"+"
1490 PRINT#6,CHR$(24)
1500 PRINTTAB(4)TSTAB(13)TTAB(23)OD
1510 NEXT ZX
1520 REM TO CONT
1530 GOTO 1310
1540 REM TO CONT
1550 PRINT#7,"                             "
1560 PRINT"                             "
1570 SLOPE=(S3Y-S4Y)/(S2X-S1X)
1580 XM=(INT(SLOPE*60000))/1000
1590 XH=(XM*60)
1600 PRINT#7,"━━━━━━━━━━━━━━ OUR =";XM;"MG/L.MIN";"━━━━━━━━";XH;"MG/L.HR"
1610 PRINT#7,"                             "
1620 PRINT"                             "
1630 PRINT#7,"                             "
1640 PRINT"                             "
1650 PRINT#7,TAB(5)"TIME"TAB(9)"TEMP"
1660 PRINTTAB(8)"TIME"TAB(25)"TEMP"
1670 PRINT#7,TAB(2)"SEC"TAB(4)"MIN"TAB(7)"C"
1680 PRINT#6,CHR$(1)
1690 PRINT#7,TAB(24)"10"TAB(3)"12"TAB(3)"14"TAB(3)"16"TAB(3)"18"TAB(3)"20"
1700 PRINT#7,TAB(54)"22"TAB(3)"24"TAB(3)"26"TAB(3)"28"TAB(3)"30"TAB(2)"32"
1710 PRINT#6,CHR$(24)
1720 PRINTTAB(4)"SEC"TAB(13)"MIN"TAB(26)"C"
1730 PRINT"                             "
1740 PRINT#7,TAB(24)"+----+----+----+----+----+----+TEMP+C-+----+----+----+"
1750 PRINT#6,CHR$(1)
1760 PRINT#7,"━━━━━━━━━━━━━━━━━━━━"
1770 PRINT#6,CHR$(24)
1780 TX=0:INPUT#5,DOM$
1790 FOR ZX=1 TO 50
1800 INPUT#15,EN$,EM$:IFEN$<>"00"GOTO1990
1810 INPUT#5,TTE$
1820 IF LEN(TTE$)<8 GOTO 1990
1830 LN=LEN(TTE$)
```

```
1840 LN=LN-7
1850 T$=LEFT$(TTE$,LN)
1860 TE$=RIGHT$(TTE$,7)
1870 TW$=RIGHT$(T$,LN-2):TS=VAL(TW$)
1880 T=(INT((VAL(TW$)/60)*100))/100
1890 TE=(INT((((VAL(TE$)/800)/0.0429)-5)*10))/10
1900 WO=INT((TE-10)*2.5)+24
1910 PRINT#1,TS,T,TE
1920 PRINT#6,CHR$(1)
1930 PRINT#7,TAB(24)"I"TAB(WO-24)"O"
1940 PRINT#6,CHR$(24)
1950 PRINTTAB(4)TSTAB(13)TTAB(24)TE
1960 NEXT ZX
1970 CLOSE5,8,5
1980 GOTO 2010
1990 CLOSE5,8,5
2000 PRINT"                    "
2010 PRINT#7,"                    "
2020 PRINT#6,CHR$(0)
2030 PRINT#7,TAB(15)"******************  END OF DATA  *************"
2040 PRINT#6,CHR$(24)
 730 IF VX=(XT+141) THEN DD$="0"
 740 IF DZ=2 THEN GOSUB 770
 750 IF DZ=1 THEN GOSUB 820
 760 GOTO 860
 770 QZ=QZ+1
 780 QZ$=STR$(QZ)
 790 NN$=QNN$+QZ$
 800 RETURN
 810 REM
 820 QX=QX+1
 830 NN$=ZNN$(QX)
 840 RETURN
 850 REM
 860 OPEN 6,4,6:CMD 6
 870 PRINT#6,CHR$(24)
 880 OPEN 7,4:OPEN 15,8,15
 890 OPEN 2,4,2
 900 OPEN 1,4,1
 910 PRINT#2,"9999"TAB(3)"999.99"TAB(4)"99.99":CLOSE2
 920 PRINT#7,TAB(7)"********** THIS IS THE DATA COLLECTED ":PRINT#6,CHR$(24)
 930 PRINT#7,TAB(7)"********** UNDER THE FILE NAME,",NN$
 940 PRINT#7,"                                                        "
 950 OPEN5,8,5,DD$+":"+NN$+",S,R"
 960 INPUT#5,DMY$:INPUT#5,HMS$
 970 INPUT#5,TT$:INPUT#5,AT$
 980 INPUT#5,MX$:INPUT#5,DR$:INPUT#5,TEMPI$:INPUT#5,COM$
 990 DMY$=RIGHT$(DMY$,6):HMS$=RIGHT$(HMS$,6)
1000 D$=LEFT$(DMY$,2):MY$=RIGHT$(DMY$,4):M$=LEFT$(MY$,2):Y$=RIGHT$(DMY$,2)
1010 HR$=RIGHT$(HMS$,6):H$=LEFT$(HR$,2):MS$=RIGHT$(HMS$,4)
1020 MT$=LEFT$(MS$,2):S$=RIGHT$(HMS$,2):TEMPI$=RIGHT$(TEMPI$,3)
1030 TT$=RIGHT$(TT$,3):AT$=RIGHT$(AT$,3):MX$=RIGHT$(MX$,3):DR$=RIGHT$(DR$,3)
1040 PRINT#6,CHR$(48)
1050 PRINT#7,"COMMENT :";COM$:PRINT#7,"  "
1060 PRINT#7,TAB(12)"THIS TEST WAS CONDUCTED ON THE, ";D$;"/";M$;"/";Y$
1070 PRINT#7,TAB(12)"THE TEST STARTED AT   (HR:MIN),  ";H$;":";MT$
1080 PRINT#7,TAB(12)"TOTAL TESTING TIME WAS, (MIN)    ";TT$
1090 PRINT#7,TAB(12)"SAMPLE WAS AERATED FOR, (MIN)    ";AT$
1100 PRINT#7,TAB(12)"SAMPLE WAS MIXED FOR,   (MIN)    ";MX$
1110 PRINT#7," ":IF QZ=1 THEN D1$=D$:M1$=M$:Y1$=Y$
1120 PRINT#7,TAB(12)"D.O  READINGS WERE TAKEN EVERY (SEC)   ";DR$
1130 PRINT#7,TAB(12)"TEMP READINGS WERE TAKEN EVERY (SEC)   ";TEMPI$
1140 PRINT#7," "
1150 PRINT#6,CHR$(50)
1160 PRINT"]"
1170 PRINT#7,TAB(5)"TIME"TAB(9)"D.O"
1180 PRINTTAB(8)"TIME"TAB(25)"D.O"
1190 PRINT#7,TAB(2)"SEC"TAB(4)"MIN"TAB(6)"MG/L"
1200 PRINT#6,CHR$(1)
1210 PRINT#7,TAB(24)"0"TAB(4)"1"TAB(4)"2"TAB(4)"3"TAB(4)"4"TAB(4)"5"TAB(4)"6"
1220 PRINT#7,TAB(59)"7"TAB(4)"8"TAB(4)"9"TAB(3)"10"TAB(3)"11"
1230 PRINT#6,CHR$(24)
1240 PRINTTAB(4)"SEC"TAB(12)"MIN"TAB(24)"MG/L"
```

```
1250 PRINT"      "
1260 PRINT#7,TAB(24)"+-----+-----+-----+-----+-----+-D.O+----MG/L----+-----+-----+-----+"
1270 PRINT#6,CHR$(1)
1280 PRINT#7,"_____"
1290 PRINT#6,CHR$(24)
1300 DX=0:INPUT#5,DOM$
1310 DX=DX+1:DX$=STR$(DX)
1320 INPUT#15,EN$,EM$:IF EN$<>"00" GOTO1540
1330 FOR ZX=1 TO 100
1340 INPUT#5,TDO$
1350 IF LEN(TDO$)<7 GOTO 1540
1360 LN=LEN(TDO$)
1370 LN=LN-3
1380 T$=LEFT$(TDO$,LN)
READY.

100 REM***********************
110 REM
120 REM    PRINTOUT PROGRAM TO PRINT
130 REM    THE D.O & TEMP DATA COLLECTED.
140 REM
150 REM    PROGRAM BY: BIJAN AIDUN
160 REM    DATE      : JAN,10,1985
170 REM***********************
180 DIM ZNN$(200):DIM SH(200):DIM ST$(200)
190 PRINT"DDDDDDO YOU WANT TO LOOK AT "
200 INPUT"THE DISK DIRACTORY Y/N";YN$
210 IF ASC(YN$)=78 GOTO 370
220 IF ASC(YN$)<>89 GOTO 190
230 INPUT"DDWHICH DISK DRIVE #";DD$
240 PRINT"DDDD$"+DD$
250 PRINT"DHIT RETURN KEY.":PRINT"D":END
260 PRINT"DDDDDDDDDDDDDDDDDDDO YOU WANT TO"
270 INPUT"GET A PRINTOUT OF YOUR FILE, OR STOP";NY$
280 IF ASC(NY$)=83THEN END
290 PRINT"DDDDDUNDER WHAT FILE NAME IS"
300 INPUT"THE DATA STORED ";QNN$
310 NN$=QNN$
320 PRINT"DDDDNOTE THE FIRST DISK HAS TO BE"
330 PRINT"IN DRIVE #0"
340 PRINT"DDDDHOW MANY OF THE DATA FILES"
350 INPUT"DARE ON THE FIRST DISK";XT
360 RETURN
370 REM CLR
380 PRINT"DDDDDDHOW MANY CONTINUOUS RUNS"
390 INPUT"DDO YOU WANT THE DATA FOR";NZ
400 IF NZ=1 GOTO 540
410 PRINT"DDDDWAS THE DATA STORED UNDER;"
420 PRINT"D  1. DIFFERENT FILE NAMES."
430 PRINT"   2. STRING OF FILE NAMES."
440 INPUT"D         TYPE THE APPROPIATE NUMBER;";DZ
450 IF DZ=2 THEN GOSUB 290:GOTO 570
460 IF DZ=1 GOTO 480
470 GOTO 380
480 FOR LZ=1 TO NZ
490 PRINT"DDDDDDNAME OF DATA FILE # ";LZ
500 INPUT"DDDDDDDDDDDDDDDDDDDDDDDDDDDD!";MM$
510 ZNN$(LZ)=MM$
520 NEXT LZ
530 NN$=ZNN$(1):GOTO 570
540 PRINT"DDDDDDUNDER WHAT FILE NAME THE"
550 INPUT"DATA IS STORED ";NN$
560 REM
570 INPUT"DDWHICH DISK DRIVE IS THE DATA DISK IN";DD$
580 PRINT"DDDDDTHE GIVEN INFORMATION IS AS SUCH"
590 PRINT"D**DATA IS STORED UNDER , ";NN$
600 PRINT"D**THE DISK IS IN DRIVE #   ";DD$
610 INPUT"DDDDO YOU WANT TO CHANGE, Y/N";Y$
620 IF ASC(Y$)=89 THEN PRINT"D":GOTO 260
630 IF ASC(Y$)<>78 GOTO 610
640 REM***********************
650 REM
660 REM     START OF PROGRAM TO
670 REM     READ & PRINTOUT DATA
```

```
680 REM*****************************
690 IF NZ=1 GOTO 860
700 QZ=0
710 FOR VX=1 TO NZ
720 IF DZ=1 GOTO 750:IF VX=(XT+1) THEN DD$="1"
3920 PRINT"⌂▓▓SUMMARY OF INPUT INFORMATION:"
3930 PRINT"▓▓▓TIME TO FILL THE SAMPLER:"TAB(28)IPTTAB(35)"MIN"
3940 PRINT"▓▓▓AERATION TIME:"TAB(28)ATTAB(35)"MIN"
3950 PRINT"▓▓▓MIXING TIME:"TAB(28)MTTAB(35)"MIN"
3960 PRINT"▓▓▓MONITORING TIME:"TAB(28)TTTAB(35)"MIN"
3970 PRINT"▓▓▓D.O READING EVERY:"TAB(28)DRTAB(35)"SEC"
3980 PRINT"▓▓▓TEMP READING EVERY:"TAB(28)TEMPITAB(35)"SEC"
3990 PRINT"▓▓DATA STORED UNDER FILE. ";NF$
4000 PRINT"▓DISK DRIVE #";DD$;"  WILL BE USED."
4010 PRINT"▓*D.O METER HAS BEEN CALIBRATED*"
4020 PRINT"▓▓DO YOU WANT TO":INPUT"CHANGE THE INPUT DATA Y/N";NY$
4030 IF ASC(NY$)=89 GOTO 3160
4040 IF ASC(NY$)<>78 THEN INPUT"TYPE IN YES OR NO";NY$:GOTO 4030
4050 PRINT"▓▓▓▓▓▓THE OPERATION HAS STARTED."
4060 IPT$=STR$(IPT)
4070 IPT=IPT*60
4080 AT$=STR$(AT)
4090 AT=(AT*60)
4100 MT$=STR$(MT)
4110 MT=(MT*60)
4120 TT$=STR$(TT)
4130 TT=(TT*60)
4140 DR$=STR$(DR)
4150 TEMPI$=STR$(TEMPI)
4160 GOTO 1260
4170 INPUT"⌂▓▓TIME TO FILL SAMPLE;   MIN";IPT
4180 INPUT"▓▓AERATION TIME;         MIN";AT
4190 INPUT"▓▓TOTAL TEST TIME;       MIN";TT
4200 INPUT"▓▓MIXING TIME;           MIN";MT
4210 INPUT"▓▓D.O READINGS EVERY;    SEC";DR
4220 INPUT"▓▓TEMP READINGS ENERY;   SEC";TEMPI
4230 GOTO 3280
3260 PRINT"⌂▓▓▓▓HOW FREQUENTLY IN SECONDS"
3270 INPUT"▓DO YOU WANT TEMPERATURE READINGS";TEMPI
3280 PRINT"⌂▓▓▓▓UNDER WHAT FILE NAME DO YOU"
3290 INPUT"▓WANT THE DATA STORED ";NF$
3300 PRINT"⌂▓▓▓▓WHAT DO YOU WANT TO DO THE NEXT RUN?"
3310 PRINT"▓▓▓▓▓▓1.) CONTINUE WITH THE SAME DATA"
3320 PRINT"▓▓▓▓2.) CHANGE THE DATA."
3330 PRINT"▓▓▓▓3.) STOP THE PROGRAM."
3340 INPUT"▓▓TYPE IN THE APPROPRIATE NUMBER";NPS
3350 IF NPS<>1 GOTO 3430
3360 PRINT"▓▓▓▓HOW MANY TIMES SHOULD THE"
3370 INPUT"▓TEST BE RUN WITH THE SAME DATA";WX
3380 PRINT"▓▓▓▓THE DATA FILE WILL BE"
3390 PRINT"▓NAMED,";NF$" 1,THROUGH,";NF$;WX
3400 NOF$=NF$
3410 NF$=NFF$+" 1"
3420 GET KY$:IF KY$="" GOTO 3420
3430 IF NPS>3 GOTO 3340
3440 IF NPS=2 THEN WZ=WZ+1:WX=0: GOTO 3460
3450 WZ=1
3460 PRINT"⌂▓▓▓▓NOTE FOR CONTINOUS RUN, FIRST DISK"
3470 PRINT"HAS TO BE IN DRIVE #0"
3480 PRINT"▓▓▓HOW MANY  DATA FILES"
3490 INPUT"▓▓DO YOU WANT STORED ON THIS DISK";XD
3500 PRINT"▓▓▓▓WHICH DISK DRIVE IS "
3510 INPUT"▓THE DATA DISK UNDER";DD$
3520 PRINT"⌂▓▓▓▓HAVE YOU CALIBRATED THE D.O METER"
3530 INPUT"▓FOR TEMPERATURE AND PRESSURE";YN$
3540 IF ASC(YN$)=89 GOTO 3920
3550 IF ASC(YN$)<>78 THEN INPUT"TYPE IN YES OR NO";YN$:GOTO3540
3560 MC=0:GOSUB 3620
3570 MC=32:GOSUB 3620
3580 PRINT"⌂▓▓▓▓DO YOU WANT TO LOOK AT TEMP."
3590 INPUT "AND CALIBRATED D.O";FF$
3600 IF FF$="Y" GOTO 3560
3610 GOTO 3920
3620 PRINT"⌂▓▓▓▓▓▓DATA TO CALIBRATE THE D.O METER."
3630 PRINT"▓▓▓▓▓▓▓▓▓▓               "
3640 BOD=0
```

```
3650 FOR A=1 TO 3
3660 POKE36876,(207+MC)
3670 POKE36876,(205+MC)
3680 FORX=0TO150:NEXTX
3690 POKE36865,00
3700 D0=(PEEK(36865)AND15):POKE36865,32
3710 D1=(PEEK(36865)AND15):POKE36865,64
3720 D2=(PEEK(36865)AND15):POKE36865,96
3730 D3=(PEEK(36865)AND15)
3740 AOD=(D3*1000)+(D2*100)+(D1*10)+D0
3750 BOD=BOD+AOD
3760 NEXT A
3770 VOD=BOD/3
3780 D3=INT(VOD/1000)
3790 D2=INT((VOD-(D3*1000))/100)
3800 D1=INT((VOD-((D3*1000)+(D2*100)))/10)
3810 D0=INT((VOD-((D3*1000)+(D2*100)+(D1*10))))
3820 IF MC=0 GOTO 3860
3830 PRINT"🬀🬀🬀🬀🬀🬀🬀🬀D.O";D3;D2;".";D1;D0
3840 GET KY$:IFKY$=""GOTO 3640
3850 RETURN
3860 DT=D3+(D2*.1)+(D1*.01)+(D0*.001)
3870 DT=DT/0.8
3880 TD=(INT(((DT/0.0429)-5)*10))/10 :TD$=STR$(TD)
3890 PRINT"🬀🬀🬀🬀🬀🬀🬀🬀TEMP";TD$;"  C  "
3900 GET KY$:IF KY$="" GOTO3640
3910 RETURN
2600 WZ=0:GOTO 2620
2610 PRINT"🬀🬀🬀DATA WERE STORED UNDER FILE; ";NF$
2620 PRINT"🬀🬀🬀ON THE DISK DRIVE #";DD$
2630 PRINT"🬀🬀🬀🬀🬀TO GET THE PRINTOUT OF DATA "
2640 PRINT"🬀🬀🬀USE BA.PRINTOUT PROGRAM AND"
2650 PRINT"🬀🬀🬀ENTER THE NAME OF FILE."
2660 PRINT"🬀🬀🬀🬀TO START THE RUN TYPE IN 'S'"
2670 GETKY$:IF KY$="S" GOTO 2690
2680 GOTO 2670
2690 RETURN
2700 REM**********************************************************
2710 REM
2720 REM
2730 REM   GET THE INFO FOR THE PROGRAM
2740 REM
2750 REM
2760 REM**********************************************************
2770 PRINT"🬀🬀🬀🬀🬀WHAT IS THE DATE TODAY?"
2780 PRINT"🬀GIVE THE INFORMATION AS DAY/MONTH/YEAR."
2790 INPUT"🬀IE. 9/JAN/85 AS 090185 ,";DMY$
2800 PRINT"🬀🬀🬀🬀TIME OF THE DAY IN 24-HR CLOCK ?"
2810 INPUT"🬀IE. FOR 1:45 PM, 134500, ";HMS$
2820 TI$=HMS$:DMY=VAL(DMY$):DMY=DMY+1000000:DMY$=STR$(DMY)
2830 HMS$="1000000"
2840 PRINT"🬀🬀🬀🬀🬀WILL THE REQUIRED INFORMATION BE GIVEN"
2850 INPUT"🬀 ON THE SCREEN OR DATA FILE";INFO$
2860 IF ASC(INFO$)=68 GOTO 2840
2870 IF ASC(INFO$)=83 GOTO 2890
2880 INPUT"******ERROR TYPE IN SCREEN OR DATA FILE";INFO$:GOTO 2860
2890 INPUT"🬀🬀🬀🬀ANY COMMENTS FOR FUTURE REFERENCE";COM$
2900 PRINT"🬀🬀🬀🬀🬀DO YOU WANT TO CALIBRATE"
2910 INPUT"🬀FOR D.O AND TEMP";CAL$
2920 IF ASC(CAL$)=78 GOTO 3000
2930 IF ASC(CAL$)<>89 GOTO 2900
2940 MC=0: GOSUB 3620
2950 MC=32:GOSUB 3620
2960 PRINT"🬀🬀🬀🬀🬀DO YOU WANT TO LOOK."
2970 INPUT"🬀AT THE CALIBRATED VALUE";H$
2980 IF ASC(H$)=89 GOTO 2940
2990 IF ASC(H$)<>78 GOTO 2960
3000 PRINT"🬀🬀🬀🬀🬀DO YOU WANT"
3010 INPUT"🬀THE QUESTIONS IN SHORT OR DETAIL";Q$
3020 IF ASC(Q$)=83 GOTO 4170
3030 IF ASC(Q$)=68 GOTO 3050
3040 GOTO 3000
3050 PRINT"🬀🬀🬀🬀🬀NOTE:"
3060 PRINT"🬀🬀🬀ACTIVATED SLUDGE WILL AUTOMATICALLY "
3070 PRINT"BE PUMPED INTO THE SAMPLER.THE AERATION"
3080 PRINT"AND MIXING OF THE SAMPLE WILL ALSO"
```

```
3090 PRINT"START AUTOMATICALLY AND CONTINUE"
3100 PRINT"AS LONG AS REQUIRED."
3110 PRINT"XDDDD.O AND TEMP READINGS WILL START"
3120 PRINT"AS SOON AS THE SAMPLER IS FULL."
3130 PRINT"THESE DATA ARE STORED AS LONG"
3140 PRINT"AND AS OFTEN AS REQUIRED"
3150 GET KY$:IF KY$="" GOTO3150
3160 PRINT":DDDDDHOW MANY MINUTES WILL IT"
3170 INPUT"XTAKE TO FILL THE SAMPLER";IPT
3180 PRINT":DDDDDHOW MANY MINUTES DO YOU WANT"
3190 INPUT"XTO AERATE THE SAMPLE";AT
3200 PRINT":DDDDDHOW MANY MINUTES DO YOU WANT"
3210 INPUT"XTO MONITOR (TOTAL TEST TIME)";TT
3220 PRINT":DDDDDHOW MANY MINUTES DO YOU"
3230 INPUT"XWANT TO MIX THE SAMPLE";MT
3240 PRINT":DDDDDHOW FREQUENTLY IN SECONDS"
3250 INPUT"XDO YOU WANT D.O READINGS";DR
1940 IF S>60 THEN M=M+1:S=S-60
1950 IF M>60 THEN H=H+1:M=M-60
1960 IF H>23 THEN DMY=VAL(DMY$)+10000:DMY$=STR$(DMY):H=H-24
1970 HMS=(H*10000)+(M*100)+S+1000000
1980 HMS$=STR$(HMS)
1990 TI$="000000"
2000 MC=32:GOSUB 570
2010 MC=0 :GOSUB 570
2020 DD=DR
2030 TM=TEMPI
2040 H1MS$=HMS$
2050 HMS=VAL(H1MS$)+VAL(TI$)
2060 H2MS$=STR$(HMS):HXMS$=RIGHT$(H2MS$,6):H$=LEFT$(HXMS$,2):H=VAL(H$)
2070 S$=RIGHT$(H2MS$,2):S=VAL(S$):MS$=RIGHT$(H2MS$,4)
2080 M=(VAL(MS$)-VAL(S$))/100
2090 IF S>59 THEN M=M+1:S=S-60
2100 IF M>59 THEN H=H+1:M=M-60
2110 IF H>23 THEN H=H-24
2120 PRINT">DDDDDDDDDDDDDDDDDDDDDDTIME OF DAY. ";H;"H:";M;"H ";S;"H     "
2130 REM
2140 IF INT(TI/60)=>AT THENXC=2:GOSUB510:XC=4: GOSUB 510
2150 REM++++SHUT OFF THE AIR VALVE & THE COMPRESSOR
2160 IF INT(TI/60)=>MT THENXC=8:GOSUB510
2170 IF INT(TI/60)=>TT THEN GOSUB 1640 :GOSUB1090:GOSUB1160:GOTO2340
2180 IF INT(TI/60)=>DD THEN GOSUB 2210
2190 IF INT(TI/60)=>TM THEN GOSUB 2250
2200 GOTO 2050
2210 IF MC=32THEN GOSUB 600:GOTO 2230
2220 MC=32:GOSUB 570
2230 DD=DD+DR
2240 RETURN
2250 IF MC=0 THEN GOSUB 600:GOTO 2270
2260 MC=0:GOSUB 570
2270 TM=TM+TEMPI
2280 RETURN
2290 REM
2300 REM++++++DISCHARGE OF++++++++++++
2310 REM+++SAMPLE AFTER TESTING++++++++
2320 REM
2330 REM
2340 XC=16:GOSUB 460
2350 IF NPS=1 GOTO 2410
2360 IF NPS=2 THEN GOSUB 2380:GOSUB 2490:GOTO2890
2370 IF NPS=3 THEN GOSUB 2380:GOSUB 2490:END
2380 FOR OU=1 TO 6500:NEXT OU
2390 POKE 36864,0
2400 RETURN
2410 REM
2420 IF WZ=WX THEN GOSUB 2380:GOSUB 2490:GOTO 2890
2430 WZ=WZ+1
2440 WZ$=STR$(WZ)
2450 NF$=NOF$+WZ$
2460 POKE 36864,16
2470 FOR OU=1 TO 6500:NEXT OU
2480 GOTO 1260
2490 REM
2500 REM+++++ PRINTOUT OF THE SUMMARY +++++
2510 REM
2520 PRINT":DDDDDTHIS IS THE END OF TEST RUN"
```

```
2530 PRINT"XXXTOTAL TEST TIME WAS"TAB(32)(TT/60)TAB(37)"MIN"
2540 PRINT"XXX0.0 READINGS COLLECTED EVERY"TAB(32)DRTAB(37)"SEC"
2550 PRINT"XXXTEMP READINGS COLLECTED EVERY"TAB(32)TEMPITAB(37)"SEC"
2560 IF WX<1 GOTO 2610
2570 PRINT"XXX**THERE WERE TOTAL OF ";WZ;" RUNS MADE"
2580 PRINT"XXXDATA WERE STORED UNDER "
2590 PRINT"XXFILE NAME,";NOF$;" 1,THROUGH,";WZ
1280 S$=RIGHT$(HMS$,2):S=VAL(S$):MS$=RIGHT$(HMS$,4)
1290 M=(VAL(LEFT$(MS$,2)))
1300 IF S>59 THEN M=M+1:S=S-60
1310 IF M>59 THEN H=H+1:M=M-60
1320 IF H>23 THEN DMY=VAL(DMY$)+10000:DMY$=STR$(DMY):H=H-24
1330 HMS=(H*10000)+(M*100)+S+1000000
1340 HMS$=STR$(HMS)
1350 TI$="000000"
1360 PRINT"]"
1370 PRINT"XXXXXXXXXXXXXXXXXXXXXTEST RUN # ";WZ
1380 NT=0:ND=0
1390 POKE 36864,0
1400 XC=16:GOSUB 460
1410 XC=1:GOSUB 460
1420 XC=32:GOSUB 460
1430 REM
1440 REM+++ OPEN UP OUTLET VALVE TO LET OUT OLD SAMPLE
1450 REM
1460 FOR BB=1 TO 5000:NEXT BB
1470 XC=16:GOSUB 510
1480 REM++++START THE AIR VALVE & THE COMPROSSER
1490 XC=2 :GOSUB 460:XC=4 :GOSUB 460
1500 XC=8:GOSUB 460
1510 REM
1520 REM+++ STORAGE OF INFO TO THE DATA FILE
1530 REM
1540 HMS=VAL(HMS$)+VAL(TI$)
1550 HYMS$=STR$(HMS):HXMS$=RIGHT$(HYMS$,6):H$=LEFT$(HXMS$,2):H=VAL(H$)
1560 S$=RIGHT$(HXMS$,2):S=VAL(S$):MS$=RIGHT$(HXMS$,4)
1570 M=(VAL(MS$)-VAL(S$))/100
1580 IF S>59 THEN M=M+1:S=S-60
1590 IF M>59 THEN H=H+1:M=M-60
1600 IF H>23 THEN DMY=VAL(DMY$)+10000:DMY$=STR$(DMY):H=H-24
1610 HMS=(H*10000)+(M*100)+S+1000000
1620 HPMS$=STR$(HMS):DMYP$=DMY$
1630 GOTO 1800
1640 IF WZ=XD+1   THEN DD$="1"
1650 IF WZ=(XD+141) THEN DD$="0"
1660 IF WZ=(XD+281) THEN DD$="1"
1670 IF WZ=(XD+421) THEN DD$="0"
1680 IF WZ=(XD+561) THEN DD$="1"
1690 IF WZ=(XD+701) THEN DD$="0"
1700 IF WZ=(XD+841) THEN DD$="1"
1710 IF WZ=(XD+981) THEN DD$="0"
1720 IF WZ=(XD+1121) THEN DD$="1"
1730 OPEN 5,8,5,DD$+":"+NF$+",S,W"
1740 PRINT#5,DMYP$:PRINT#5,HPMS$:PRINT#5,TT:PRINT#5,AT$:PRINT#5,MT$
1750 PRINT#5,DR$:PRINT#5,TEMPI$:PRINT#5,COM$
1760 RETURN
1770 REM
1780 REM++++++SHUT DOWN ALL THE CIRCUITS++++++++
1790 REM
1800 IF INT(TI/60)<IPT GOTO 1800
1810 XC=1:GOSUB 510
1820 XC=32:GOSUB 510
1830 REM
1840 REM+++++START THE DO READING+++++++++
1850 REM+++++STOP AERATION & MIXING++
1860 REM
1870 REM
1880 PRINT"]"
1890 PRINT"XXXXXXXXXXXXXXXXXXXXXTEST RUN # ";WZ
1900 HMS=VAL(HMS$)+VAL(TI$)
1910 HMS$=STR$(HMS):HXMS$=RIGHT$(HMS$,6):H$=LEFT$(HXMS$,2):H=VAL(H$)
1920 S$=RIGHT$(HMS$,2):S=VAL(S$):MS$=RIGHT$(HMS$,4)
1930 M=(VAL(MS$)-VAL(S$))/100
```

```
620 POKE36876,(207+MC)
630 REM**SET CA2 LO $CD
640 POKE36876,(205+MC)
650 REM**CHECK FOR CON.COMPLETE CC
660 FOR X=0 TO 150:NEXT X
670 REM**LOAD IN DATA
680 POKE36865,00
690 D0=(PEEK(36865)AND15):POKE36865,32
700 D1=(PEEK(36865)AND15):POKE36865,64
710 D2=(PEEK(36865)AND15):POKE36865,96
720 D3=(PEEK(36865)AND15)
730 AOD=(D3*1000)+(D2*100)+(D1*10)+D0
740 BOD=BOD+AOD
750 NEXT A
760 VOD=BOD/3
770 D3=INT(VOD/1000)
780 D2=INT((VOD-(D3*1000))/100)
790 D1=INT((VOD-((D3*1000)+(D2*100)))/10)
800 D0=INT((VOD-((D3*1000)+(D2*100)+(D1*10))))
810 REM
820 REM+++++ PRINT THE RECORDED DATA.+++++
830 REM
840 IF MC=0 GOTO 950
850 T=(INT((TI/3600)*100))/100
860 PRINT"{ }
870 PRINT"{ }TIME;(MIN)";T;"{ }D.0   ";D3;D2;".";D1;D0
880 D3$=STR$(D3):D2$=STR$(D2):D1$=STR$(D1):D0$=STR$(D0)
890 D$=D3$+D2$+"."+D1$+D0$
900 DX=DX+1
910 T$=STR$(INT(TI/60))
920 DR$(DX)=T$+D$
930 REM TO CONTINUE
940 RETURN
950 DT=D3+(D2*.1)+(D1*.01)+(D0*.001)
960 DT=DT/0.8
970 TD=(INT(((DT/0.0429)-5)*10))/10 :TD$=STR$(TD)
980 T=(INT((TI/3600)*100))/100
990 PRINT"{ }
1000 PRINT"{ }TIME;(MIN)";T;"  TEMPERATURE   ";TD$;"  C  "
1010 D3$=STR$(D3):D2$=STR$(D2):D1$=STR$(D1):D0$=STR$(D0)
1020 TD$=D3$+D2$+D1$+D0$
1030 TX=TX+1
1040 T$=STR$(INT(TI/60))
1050 TR$(TX)=T$+TD$
1060 REM TO CONTINUE
1070 RETURN
1080 REM
1090 REM+++++++ STORE DO & TEMP +++++++
1100 REM
1110 REM TO CONTINUE
1120 REM TO CONTINUE
1130 DX=DX+1:DR$(DX)="999"
1140 FOR ZX=0TODX:PRINT#5,DR$(ZX):NEXTZX
1150 DX=0:RETURN
1160 REM TO CONTINUE
1170 REM TO CONTINUE
1180 TX=TX+1:TR$(TX)="999"
1190 FORZX=0 TOTX:PRINT#5,TR$(ZX):NEXTZX
1200 CLOSE 5,8,5:TX=0:RETURN
1210 REM*********************************************************
1220 REM
1230 REM      OPERATION PROGRAM
1240 REM
1250 REM*********************************************************
1260 HMS=VAL(HMS$)+VAL(TI$)
1270 HMS$=STR$(HMS):HXMS$=RIGHT$(HMS$,6):H$=LEFT$(HXMS$,2):H=VAL(H$)
READY.

10 REM***********************************************************
*
20 REM
30 REM     THE PROGRAM TO OPERATE THE
40 REM     OXYGEN UPTAKE RATE DEVICE.
50 REM     MEASURES AND RECORDS THE DO
60 REM     AND TEMPERATURE OF AN
70 REM     ACTIVATED SLUDGE SAMPLE.
```

```
80 REM    THE COLLECTED DATA IS THEN
90 REM    STORED.
100 REM
110 REM   PROGRAM BY: BIJAN AIDUN.
120 REM   DATE      : JAN 9 1985
130 REM
140 REM*********************************************************************
150 REM
160 REM+++++++++SET UP VIA++++++++++
170 REM
180 DIM DR$(200):DIM TR(100)
190 REM DDRA SET TO $F0 1=OUT 0=IN
200 POKE36867,240:POKE36866,255:POKE36864,0
210 REM DRA SET ALL OUTPUTS TO 0
220 POKE36865,0
230 REM PCR SET CA1,CA2,CB2,$CD
240 POKE36876,205
250 REM IER SET IRQ FLAG ON CA1CLOSE$82
260 POKE36878,130
270 REM
280 REM+++ GO TO START OF THE PROGRAM. +++
290 REM
300 GOTO 63999
310 REM
320 REM*********************************************************************
330 REM
340 REM     ALL THE SUBROUTINES IN THE
350 REM     PROGRAM ARE STORED HERE AT
360 REM     THE BEGINNING TO SPEED UP THE
370 REM     OPERATION PROCESS.
380 REM        LINE#300    OPEN CIRCUT
390 REM        LINE#350    CLOSE CIRCUT
400 REM        LINE#400    READ DO & TEMP
410 REM        LINE#700    STOR DO & TEMP
420 REM
430 REM
440 REM
450 REM******************************
460 P=PEEK(36864)
470 P1=P AND XC
480 IF P1=1 THEN RETURN
490 P=P+XC:POKE36864,P
500 RETURN
510 P=PEEK(36864)
520 P1=P AND XC
530 IF P1=0 THEN RETURN
540 P=P-XC:POKE36864,P
550 RETURN
560 REM
570 REM**SET CA2 HI $CF
580 POKE 36876,(205+MC)
590 FOR WA=0 TO 1500 :NEXT WA
600 BOD=0:BET=0
610 FOR A=1 TO 3
```

The embodiments of the invention in which an exclusive property or privilege is claimed are defined as follows:

1. A method of controlling the aeration rate of an activated sludge wastewater treatment tank, comprising the steps:
    (a) withdrawing a sample of mixed liquor and suspended solids from the tank into a chamber in which is located a dissolved oxygen probe that outputs a signal which is a function of the amount of dissolved oxygen in the liquid adjacent the probe,
    (b) aerating the sample, then arresting the aeration,
    (c) using a computer to sample the signal at regular intervals after aeration has ceased, and to produe a set of time-separated values corresponding to the sampled signals, which values represent the dissolved oxygen in the sample of liquid at timed intervals,
    (d) emptying the chamber of its contents,
    (e) repeating the steps (a) to (d) a plurality of times to generate a plurality of sets of said values,
    (f) using computer means to calculate, for each set of said values, the rate at which the oxygen content of the sample decreases with time, and
    (g) whenever, for any set, the rate of decrease of the oxygen content is below a predetermined value, decreasing the said aeration rate.

2. The method claimed in claim 1, which further includes using said computer means to print out, for each set of values, a table showing each value and the time to which it corresponds.

3. The method claimed in claim 1, which further includes using said computer means to plot, for each set of values, a graph of the values versus the corresponding times when the digital signal is sampled.

4. The invention claimed in claim 1, in which the decrease of the said aeration rate is accomplished by regulating the on-off time of air blowers arranged to blow air into the wastewater treatment tank.

5. The invention claimed in claim 1, in which the decrease of the said aeration rate is accomplished by reducing the speed of air blowers blowing air into the said wastewater treatment tank.

6. The invention claimed in claim 1, in which the signal is an analog signal, the method further including the step of converting the analog signal to a digital signal prior to being sampled by the computer.

7. In a wastewater treatment process utilizing a treatment tank having an upstream end for the entry of wastewater to be treated and a downstream end for the exit of wastewater, the tank containing activated sludge incorporating bacterial agents which function to break down organic materials in the wastewater, a method of controlling the rate at which activated sludge is removed from said downstream end and readmitted to the tank at the upstream end thereof, the method comprising the steps:

(a) withdrawing a sample of mixed liquor and suspended solids from the tank into a chamber in which is located a dissolved oxygen probe that outputs a signal which is a function of the amount of dissolved oxygen in the sample adjacent the probe, (b) aerating the ample, then arresting the aeration, (c) using a computer to sample the signal at regular intervals after aeration has ceased, and to produce a set of time-separated values corresponding to the sampled signals, which values represent the dissolved oxygen in the sample at timed intervals, (d) emptying the chamber of its contents, (e) repeating the steps (a) to (d) a plurality of times to generate a plurality of sets of said values, (f) using computer means to calculate, for each set of said values, the rate at which the oxygen content of the sample decreases with time, and (g) whenever, for any set, the rate of decreases of the oxygen content is below a predetermined value, increasing the rate at which activatd sludge is passed from said downstream to said upstream end.

8. The invention claimed in claim 7, which further includes using said computer means to print out, for each set of values, a table showing each value and the time to which it corresponds.

9. The invention claimed in claim 7, which further includes using said computer means to plot, for each set of values, a graph of the values versus the corresponding times when the signal is sampled.

10. The invention claimed in claim 7, in which the signal is an analog signal, the method including the conversion of the analog signal to a digital signal prior to being sampled by the computer.

* * * * *